(12) United States Patent
Huebner et al.

(10) Patent No.: US 9,414,871 B2
(45) Date of Patent: *Aug. 16, 2016

(54) BONE PLATES WITH MOVABLE LOCKING ELEMENTS

(71) Applicant: Acumed LLC, Hillsboro, OR (US)

(72) Inventors: Randall J. Huebner, Portland, OR (US); David G. Jensen, Hillsboro, OR (US)

(73) Assignee: Acumed LLC, Hillsboro, OR (US)

( * ) Notice: Subject to any disclaimer, the term of this patent is extended or adjusted under 35 U.S.C. 154(b) by 165 days.

This patent is subject to a terminal disclaimer.

(21) Appl. No.: 13/652,185

(22) Filed: Oct. 15, 2012

(65) Prior Publication Data

US 2013/0090656 A1  Apr. 11, 2013

Related U.S. Application Data

(63) Continuation of application No. 12/768,508, filed on Apr. 27, 2010, now abandoned, and a continuation-in-part of application No. 13/246,687, filed on Sep. 27, 2011, now Pat. No. 8,518,090, and a (Continued)

(51) Int. Cl.
*A61B 17/80*  (2006.01)
*A61B 17/17*  (2006.01)

(52) U.S. Cl.
CPC ......... *A61B 17/8052* (2013.01); *A61B 17/1728* (2013.01); *A61B 17/1735* (2013.01); *A61B 17/80* (2013.01); *A61B 17/808* (2013.01); *A61B 17/8061* (2013.01); *A61B 17/8085* (2013.01); *A61B 17/8004* (2013.01); *A61B 2017/1782* (2013.01)

(58) Field of Classification Search
CPC ........... A61B 17/7058; A61B 17/7059; A61B 17/58; A61B 17/7014; A61B 17/80; A61B 17/8047; A61B 17/8695
USPC .................. 606/283, 284, 286, 289, 290, 294
See application file for complete search history.

(56) References Cited

U.S. PATENT DOCUMENTS

| | | | |
|---|---|---|---|
| 4,382,790 A * | 5/1983 | Loge et al. | 433/126 |
| 4,513,744 A | 4/1985 | Klaue | |
| 4,943,292 A | 7/1990 | Foux | |
| 4,957,497 A | 9/1990 | Hoogland et al. | |
| 5,129,899 A | 7/1992 | Small et al. | |
| 5,709,686 A * | 1/1998 | Talos | A61B 17/8057 606/280 |
| 5,735,853 A | 4/1998 | Olerud | |

(Continued)

FOREIGN PATENT DOCUMENTS

| AU | 2006267081 B2 | 10/2011 |
|---|---|---|
| CA | 2353586 A1 | 6/2000 |

(Continued)

OTHER PUBLICATIONS

Kolodziej, Patricia MD, Biomechanical Evaluation of the Schuli Nut, Clinic Orthopaedics and Related Research, vol. 347 pp. 79-85, Feb. 1998, 9 pages.

(Continued)

*Primary Examiner* — Anu Ramana
(74) *Attorney, Agent, or Firm* — Kolisch Hartwell, P.C.

(57) ABSTRACT

System, including methods, apparatus, and kits, for fixing bones with bone plates having movable locking elements.

13 Claims, 6 Drawing Sheets

Related U.S. Application Data continuation-in-part of application No. 13/246,690, filed on Sep. 27, 2011, now Pat. No. 8,523,919, and a continuation-in-part of application No. 13/246,684, filed on Sep. 27, 2011, now Pat. No. 8,425,575, and a continuation-in-part of application No. 13/187,395, filed on Jul. 20, 2011, now abandoned, said application No. 12/768,508 is a continuation-in-part of application No. 11/504,223, filed on Aug. 14, 2006, now Pat. No. 7,704,251, and a continuation-in-part of application No. 11/637,626, filed on Dec. 11, 2006, now Pat. No. 7,717,945, and a continuation-in-part of application No. 11/929,026, filed on Oct. 30, 2007, now Pat. No. 7,955,388, and a continuation-in-part of application No. 12/175,223, filed on Jul. 17, 2008, now Pat. No. 8,475,504, and a continuation-in-part of application No. 12/176,913, filed on Jul. 21, 2008, now Pat. No. 8,231,627, said application No. 11/504,223 is a continuation-in-part of application No. 10/716,719, filed on Nov. 19, 2003, now Pat. No. 7,090,676, said application No. 11/637,626 is a continuation-in-part of application No. 10/625,503, filed on Jul. 22, 2003, now Pat. No. 7,537,603, and a continuation-in-part of application No. 10/712,202, filed on Nov. 12, 2003, now abandoned, and a continuation-in-part of application No. 10/717,015, filed on Nov. 19, 2003, now Pat. No. 7,537,604, and a continuation-in-part of application No. 10/717,399, filed on Nov. 19, 2003, now Pat. No. 7,326,212, and a continuation-in-part of application No. 10/717,401, filed on Nov. 19, 2003, now Pat. No. 7,153,309, and a continuation-in-part of application No. 10/717,402, filed on Nov. 19, 2003, now Pat. No. 7,189,237, and a continuation-in-part of application No. 10/734,017, filed on Dec. 10, 2003, now Pat. No. 7,147,640, and a continuation-in-part of application No. 10/873,522, filed on Jun. 21, 2004, now Pat. No. 7,537,596, and a continuation-in-part of application No. 10/993,205, filed on Nov. 18, 2004, now Pat. No. 7,235,079, and a continuation-in-part of application No. 11/050,342, filed on Feb. 2, 2005, now abandoned, and a continuation-in-part of application No. 11/109,984, filed on Apr. 19, 2005, now Pat. No. 7,578,825, and a continuation-in-part of application No. 11/109,985, filed on Apr. 19, 2005, now abandoned, and a continuation-in-part of application No. 11/112,858, filed on Apr. 22, 2005, now abandoned, and a continuation-in-part of application No. 11/273,811, filed on Nov. 14, 2005, now abandoned, and a continuation-in-part of application No. 11/274,597, filed on Nov. 14, 2005, now Pat. No. 7,927,332, and a continuation-in-part of application No. 11/330,802, filed on Jan. 11, 2006, now abandoned, and a continuation-in-part of application No. 11/413,631, filed on Apr. 28, 2006, now Pat. No. 8,652,142, and a continuation-in-part of application No. 11/449,554, filed on Jun. 7, 2006, now abandoned, and a continuation-in-part of application No. 11/486,959, filed on Jul. 13, 2006, now Pat. No. 7,857,836, and a continuation-in-part of application No. 11/504,223, filed on Aug. 14, 2006, now Pat. No. 7,704,251, and a continuation-in-part of application No. 11/550,255, filed on Oct. 17, 2006, now Pat. No. 8,231,662, and a continuation-in-part of application No. 11/585,378, filed on Oct. 23, 2006, now Pat. No. 7,914,532, said application No. 11/449,554 is a continuation of application No. 10/873,522, filed on Jun. 21, 2004, now Pat. No. 7,537,596.

(60) Provisional application No. 60/427,908, filed on Nov. 19, 2002, provisional application No. 60/512,136, filed on Oct. 17, 2003, provisional application No. 60/398,075, filed on Jul. 22, 2002, provisional application No. 60/484,262, filed on Jun. 30, 2003, provisional application No. 60/512,323, filed on Oct. 17, 2003, provisional application No. 60/512,136, filed on Oct. 17, 2003, provisional application No. 60/427,910, filed on Nov. 19, 2002, provisional application No. 60/512,322, filed on Oct. 17, 2003, provisional application No. 60/427,908, filed on Nov. 19, 2002, provisional application No. 60/454,217, filed on Mar. 12, 2003, provisional application No. 60/480,529, filed on Jun. 20, 2003, provisional application No. 60/541,414, filed on Feb. 2, 2004, provisional application No. 60/563,860, filed on Apr. 19, 2004, provisional application No. 60/563,767, filed on Apr. 19, 2004, provisional application No. 60/564,853, filed on Apr. 22, 2004, provisional application No. 60/627,297, filed on Nov. 12, 2004, provisional application No. 60/627,721, filed on Nov. 12, 2004, provisional application No. 60/480,529, filed on Jun. 20, 2003, provisional application No. 60/699,277, filed on Jul. 13, 2005, provisional application No. 60/729,373, filed on Oct. 21, 2005, provisional application No. 60/856,128, filed on Nov. 1, 2006, provisional application No. 60/961,317, filed on Jul. 19, 2007, provisional application No. 61/390,121, filed on Oct. 5, 2010, provisional application No. 61/386,921, filed on Sep. 27, 2010, provisional application No. 61/386,925, filed on Sep. 27, 2010.

(56) References Cited

U.S. PATENT DOCUMENTS

| | | |
|---|---|---|
| 5,741,258 A | 4/1998 | Klaue et al. |
| 5,931,838 A | 8/1999 | Vito |
| 6,224,602 B1 * | 5/2001 | Hayes ................ A61B 17/7059 606/280 |
| 6,280,445 B1 | 8/2001 | Morrison et al. |
| 6,302,883 B1 | 10/2001 | Bono |
| 6,315,779 B1 | 11/2001 | Morrison et al. |
| 6,503,250 B2 | 1/2003 | Paul |
| 6,540,746 B1 | 4/2003 | Bühler et al. |
| 6,663,632 B1 | 12/2003 | Frigg |
| 6,695,846 B2 * | 2/2004 | Richelsoph et al. ............ 606/71 |
| 6,719,759 B2 | 4/2004 | Wagner et al. |
| 6,858,031 B2 | 2/2005 | Morrison et al. |
| 7,048,739 B2 * | 5/2006 | Konieczynski et al. ...... 606/288 |
| 7,090,676 B2 | 8/2006 | Huebner et al. |
| 7,147,640 B2 | 12/2006 | Huebner et al. |
| 7,153,309 B2 | 12/2006 | Huebner et al. |
| 7,189,237 B2 | 3/2007 | Huebner |
| 7,235,079 B2 | 6/2007 | Jensen et al. |
| 7,326,212 B2 | 2/2008 | Huebner |
| 7,537,596 B2 | 5/2009 | Jensen |
| 7,537,603 B2 | 5/2009 | Huebner et al. |
| 7,537,604 B2 | 5/2009 | Huebner |
| 7,578,825 B2 | 8/2009 | Huebner |
| 7,704,251 B2 | 4/2010 | Huebner et al. |
| 7,717,945 B2 | 5/2010 | Jensen et al. |
| 7,857,836 B2 | 12/2010 | Huebner et al. |
| 7,914,532 B2 | 3/2011 | Shaver et al. |
| 7,927,332 B2 | 4/2011 | Huebner et al. |
| 7,955,388 B2 | 6/2011 | Jensen et al. |
| 8,043,346 B2 * | 10/2011 | Markworth ................... 606/294 |
| 8,231,627 B2 | 7/2012 | Huebner et al. |
| 8,231,662 B2 | 7/2012 | Huebner |
| 2004/0092939 A1 | 5/2004 | Freid et al. |
| 2004/0102776 A1 | 5/2004 | Huebner |
| 2004/0267261 A1 | 12/2004 | Derouet |
| 2005/0015131 A1 * | 1/2005 | Fourcault et al. ............. 607/116 |

(56) References Cited

U.S. PATENT DOCUMENTS

| | | |
|---|---|---|
| 2005/0049593 A1 | 3/2005 | Duong et al. |
| 2006/0198110 A1 | 9/2006 | Hunkeler et al. |
| 2007/0055251 A1 | 3/2007 | Huebner et al. |

FOREIGN PATENT DOCUMENTS

| | | |
|---|---|---|
| CN | 101262828 B | 6/2011 |
| EP | 1656896 A2 | 5/2006 |
| EP | 1906850 B1 | 4/2013 |
| GB | 2442189 B | 11/2010 |
| JP | 2004-313514 | 11/2004 |
| KR | 101318537 B1 | 10/2013 |
| WO | 9416634 A1 | 8/1994 |
| WO | 9632071 A1 | 10/1996 |
| WO | 03055401 A1 | 7/2003 |
| WO | 2007009124 A2 | 1/2007 |

OTHER PUBLICATIONS

An, Yuehuei H. M.D., Internal Fixation in Osteoporotic Bone, Current Methods in Fixation of Osteoporotic Bone, Thieme Medical Publishers, 2002, 3 pages.

Copenheaver, Blaine R., Authorized officer, International Searching Authority, International Search Report, International Patent Application Serial No. PCT/US2006/027805; search date: Dec. 12, 2006; mailed Jan. 31, 2007; 2 pages.

Copenheaver, Blaine R., Authorized officer, International Searching Authority, Written Opinion of the International Searching Authority, International Patent Application Serial No. PCT/US2006/027805; opinion completion date: Dec. 12, 2006; mailed Jan. 31, 2007; 4 pages.

The State Intellectual Property Office of the People's Republic of China, First Office Action, Chinese Patent Application No. 2006800334275; Nov. 27, 2009; 9 pages.

European Patent Office, Extended European Search Report, European Patent Application Serial No. EP06787678; search completion date: Feb. 11, 2010; mailed Feb. 26, 2010; 7 pages.

United Kingdom Intellectual Property Office, Examination Report regarding Application Serial No. GB0802606.4; dated Apr. 30, 2010; 1 page.

The State Intellectual Property Office of the People's Republic of China, Second Office Action, Chinese Patent Application No. 2006800334275; Jul. 7, 2010; 5 pages.

European Patent Office, Examination Report, European Patent Application Serial No. EP06787678; dated Jul. 8, 2010; 5 pages.

The State Intellectual Property Office of the People's Republic of China, Third Office Action, Chinese Patent Application No. 2006800334275; Oct. 27, 2010; 5 pages.

European Patent Office, Examination Report, European Patent Application Serial No. EP06787678; dated Jul. 4, 2011; 4 pages.

Japan Patent Office, Office Action, Japanese Application Serial No. 2008-521716; Oct. 26, 2011; 7 pages.

European Patent Office, Examination Report, European Patent Application Serial No. EP06787678; dated Nov. 17, 2011; 4 pages.

Japan Patent Office, Second Office Action, Japanese Application Serial No. 2008-521716; Aug. 13, 2012; 3 pages.

\* cited by examiner

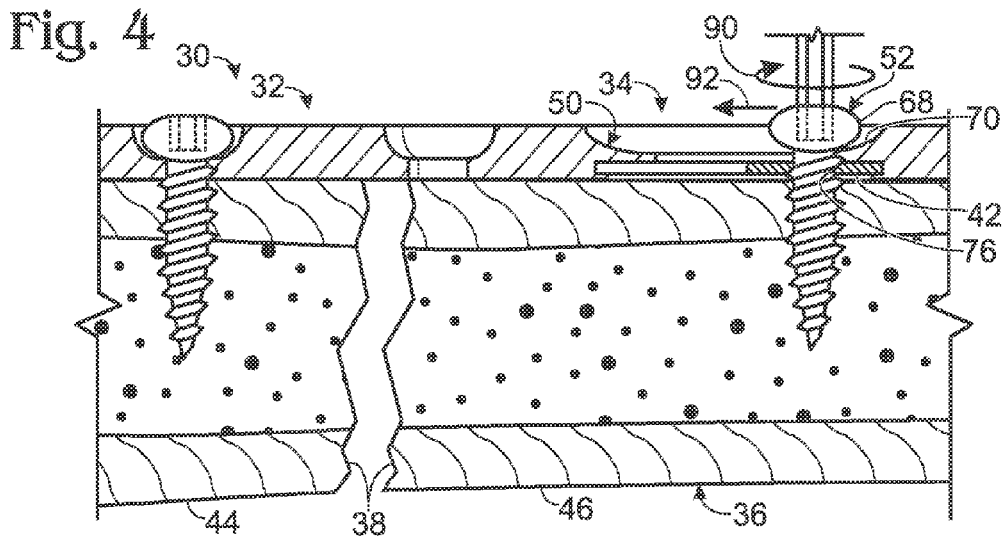
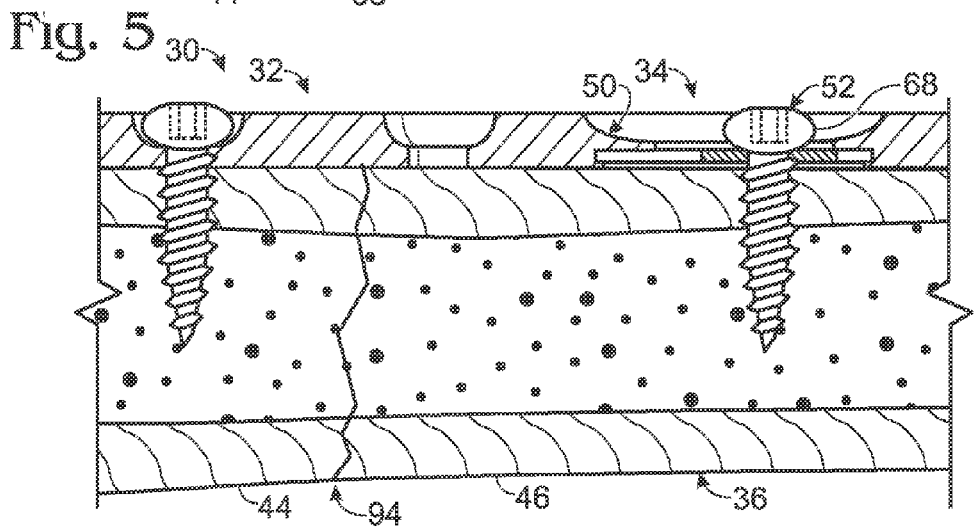
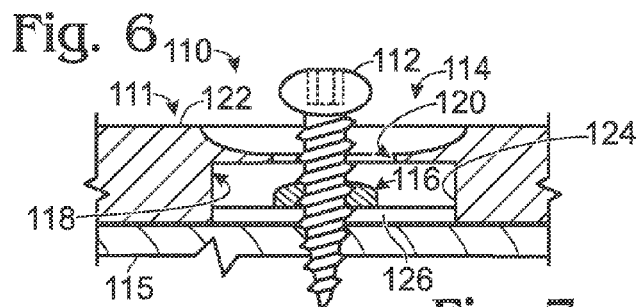
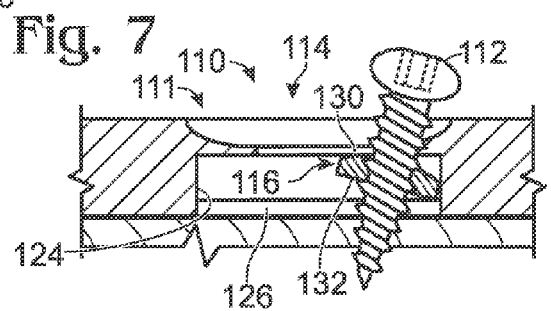

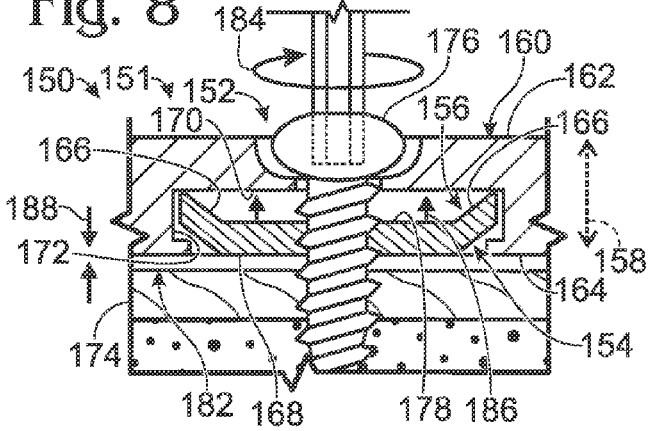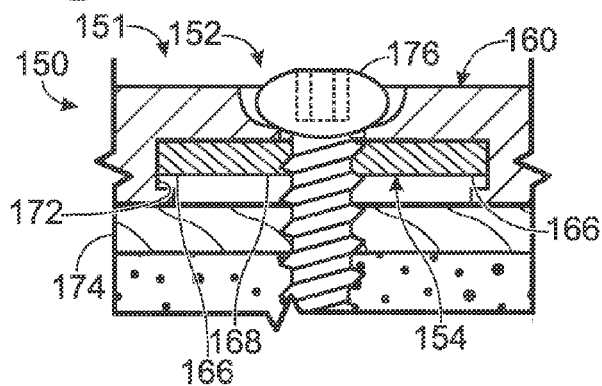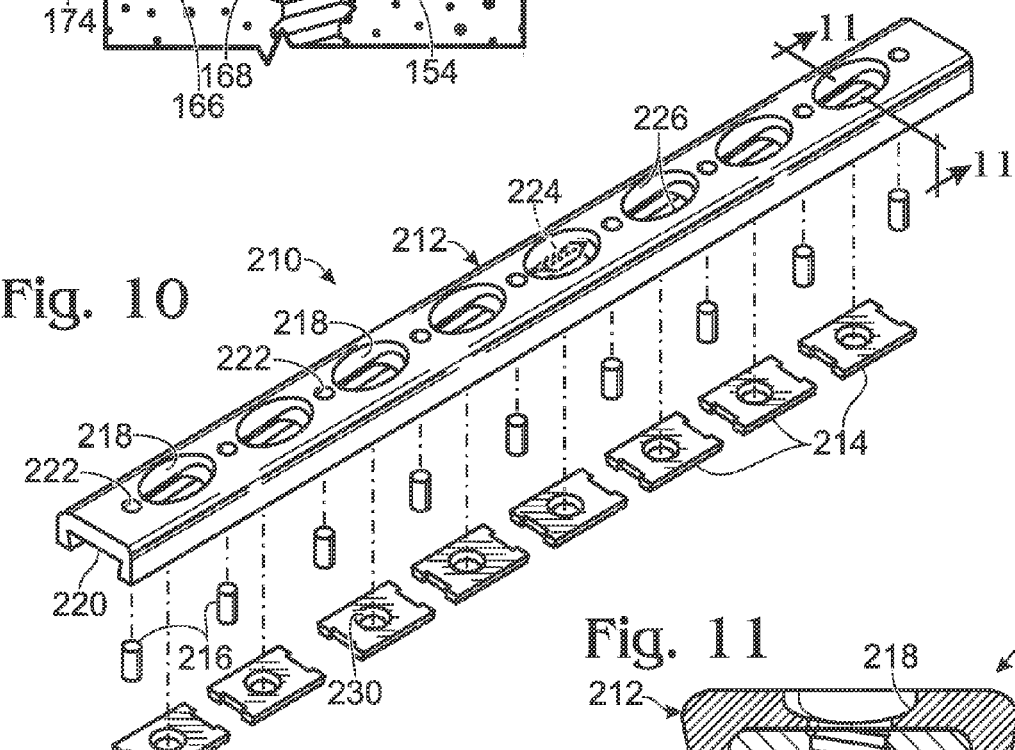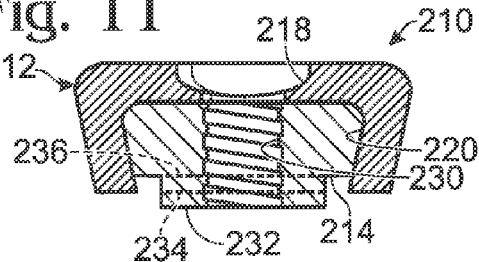

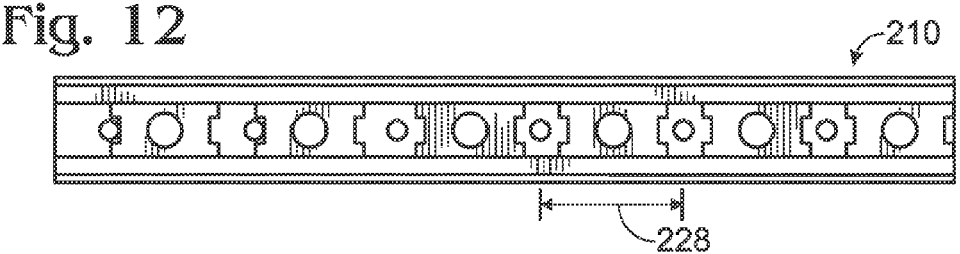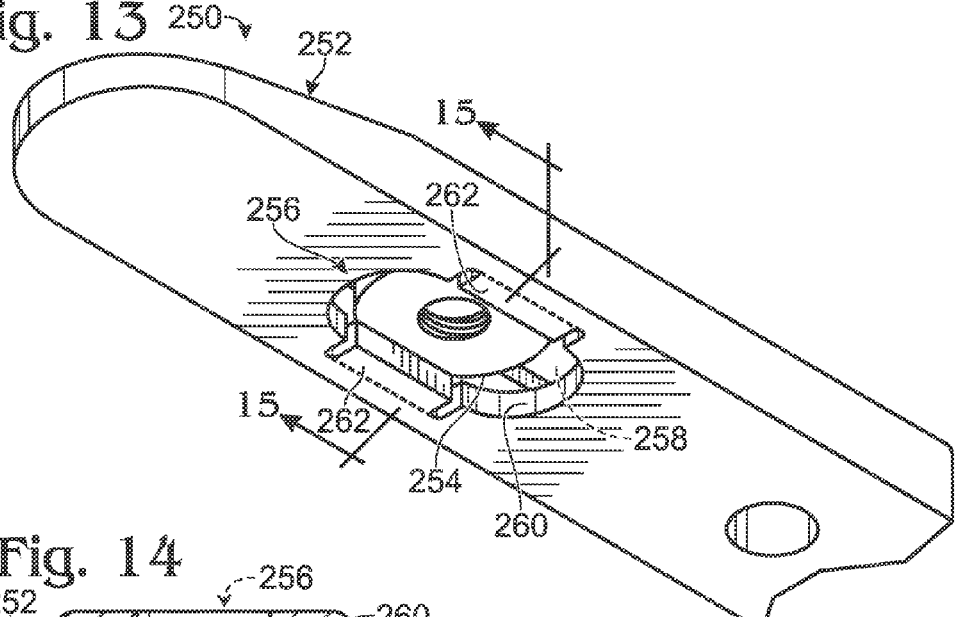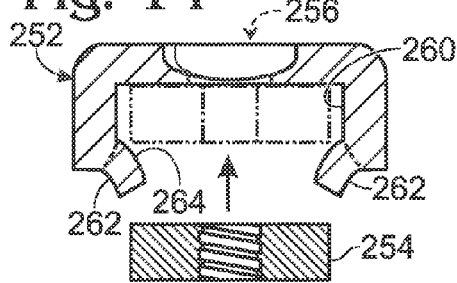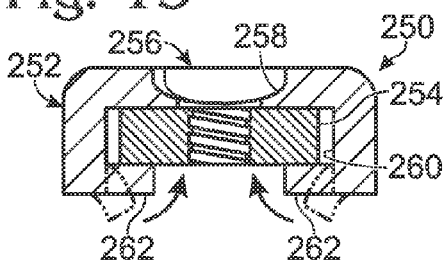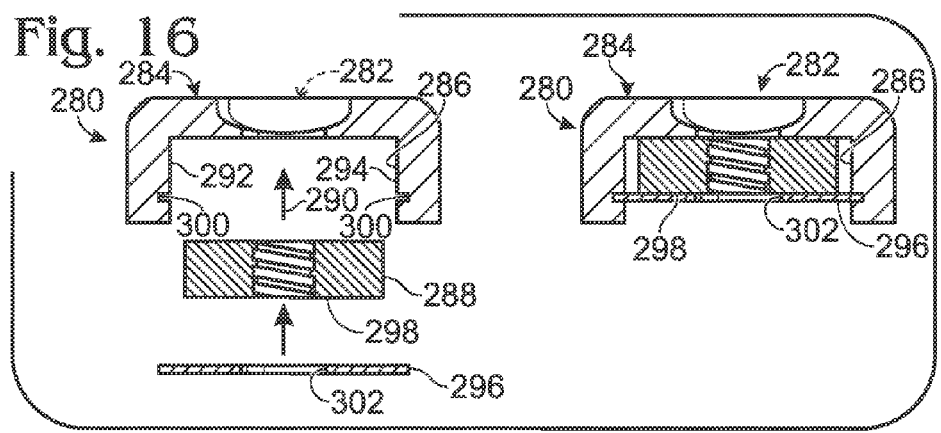

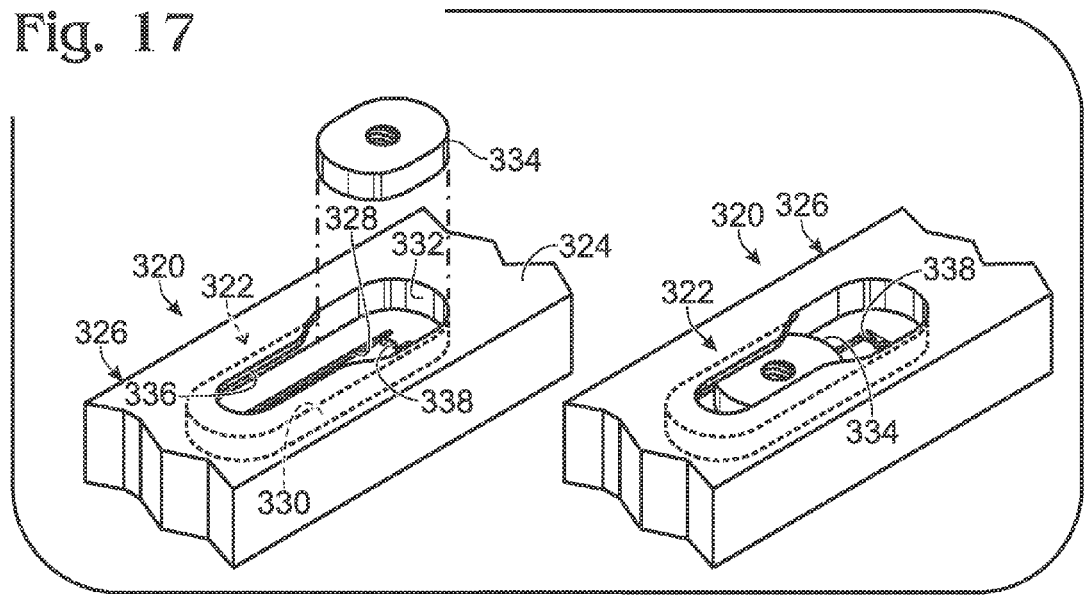
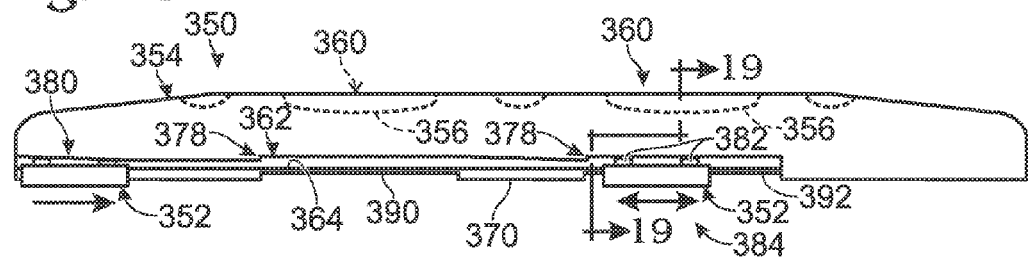
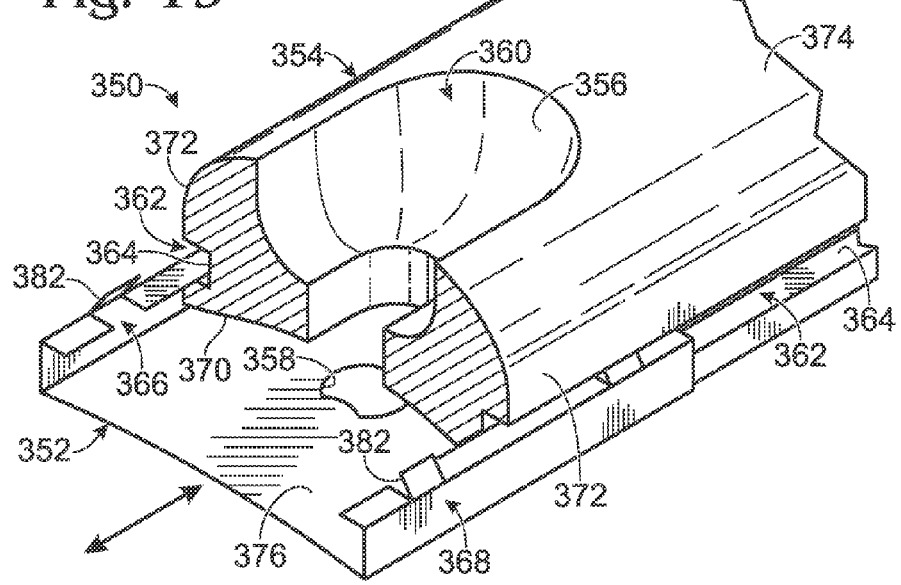

BONE PLATES WITH MOVABLE LOCKING ELEMENTS

This application is a continuation of U.S. patent application Ser. No. 12/768,508, filed Apr. 27, 2010, now abandoned, and is a continuation-in-part of the following U.S. patent applications: Ser. No. 13/246,687, filed Sep. 27, 2011, now U.S. Pat. No. 8,518,090; Ser. No. 13/246,690, filed Sep. 27, 2011, now U.S. Pat. No. 8,523,919; Ser. No. 13/246,684, filed Sep. 27, 2011, now U.S. Pat. No. 8,425,575; and Ser. No. 13/187,395, filed Jul. 20, 2011, now abandoned.

U.S. patent application Ser. No. 12/768,508, in turn, is a continuation-in-part of the following U.S. patent applications: Ser. No. 11/504,223, filed Aug. 14, 2006, now U.S. Pat. No. 7,704,251; Ser. No. 11/637,626, filed Dec. 11, 2006, now U.S. Pat. No. 7,717,945; Ser. No. 11/929,026, filed Oct. 30, 2007, now U.S. Pat. No. 7,955,388; Ser. No. 12/175,223, filed Jul. 17, 2008, now U.S. Pat. No. 8,475,504; and Ser. No. 12/176,913, filed Jul. 21, 2008, now U.S. Pat. No. 8,231,627.

U.S. patent application Ser. No. 11/504,223, in turn, is a continuation of U.S. patent application Ser. No. 10/716,719, filed Nov. 19, 2003, now U.S. Pat. No. 7,090,676, which, in turn, is based upon and claims the benefit under 35 U.S.C. §119(e) of the following U.S. provisional patent applications: Ser. No. 60/427,908, filed Nov. 19, 2002, and Ser. No. 60/512,136, filed Oct. 17, 2003.

U.S. patent application Ser. No. 11/637,626, in turn, is a continuation-in-part of the following U.S. patent applications: Ser. No. 10/625,503, filed Jul. 22, 2003, now U.S. Pat. No. 7,537,603; Ser. No. 10/712,202, filed Nov. 12, 2003, now abandoned; Ser. No. 10/717,015, filed Nov. 19, 2003, now U.S. Pat. No. 7,539,604; Ser. No. 10/717,399, filed Nov. 19, 2003, now U.S. Pat. No. 7,326,212; Ser. No. 10/717,401, filed Nov. 19, 2003, now U.S. Pat. No. 7,153,309; Ser. No. 10/717,402, filed Nov. 19, 2003, now U.S. Pat. No. 7,189,237; Ser. No. 10/734,017, filed Dec. 10, 2003, now U.S. Pat. No. 7,147,640; Ser. No. 10/873,522, filed Jun. 21, 2004, now U.S. Pat. No. 7,537,596; Ser. No. 10/993,205, filed Nov. 18, 2004, now U.S. Pat. No. 7,235,079; Ser. No. 11/050,342, filed Feb. 2, 2005, now abandoned; Ser. No. 11/109,984, filed Apr. 19, 2005, now U.S. Pat. No. 7,578,825; Ser. No. 11/109,985, filed Apr. 19, 2005, now abandoned; Ser. No. 11/112,858, filed Apr. 22, 2005, now abandoned; Ser. No. 11/273,811, filed Nov. 14, 2005, now abandoned; Ser. No. 11/274,597, filed Nov. 14, 2005, now U.S. Pat. No. 7,927,332; Ser. No. 11/330,802, filed Jan. 11, 2006, now abandoned; Ser. No. 11/413,631, filed Apr. 28, 2006, now U.S. Pat. No. 8,652,142; Ser. No. 11/449,554, filed Jun. 7, 2006, now abandoned; Ser. No. 11/486,959, filed Jul. 13, 2006, now U.S. Pat. No. 7,857,836; Ser. No. 11/504,223, filed Aug. 14, 2006, now U.S. Pat. No. 7,704,251; Ser. No. 11/550,255, filed Oct. 17, 2006, now U.S. Pat. No. 8,231,662; and Ser. No. 11/585,378, filed Oct. 23, 2006, now U.S. Pat. No. 7,914,532.

U.S. patent application Ser. No. 10/625,503, in turn, is based upon and claims the benefit under 35 U.S.C. §119(e) of the following U.S. provisional patent applications: Ser. No. 60/398,075, filed Jul. 22, 2002, and Ser. No. 60/484,262, filed Jun. 30, 2003.

U.S. patent application Ser. No. 10/717,015, in turn, is based upon and claims the benefit under 35 U.S.C. §119(e) of U.S. provisional patent application Ser. No. 60/512,323, filed Oct. 17, 2003.

U.S. patent application Ser. No. 10/717,399, in turn, is based upon and claims the benefit under 35 U.S.C. §119(e) of the following U.S. provisional patent applications: Ser. No. 60/427,908, filed Nov. 19, 2002, and Ser. No. 60/512,136, filed Oct. 17, 2003.

U.S. patent application Ser. No. 10/717,401, in turn, is based upon and claims the benefit under 35 U.S.C. §119(e) of the following U.S. provisional patent applications: Ser. No. 60/427,910, filed Nov. 19, 2002, and Ser. No. 60/512,322, filed Oct. 17, 2003.

U.S. patent application Ser. No. 10/717,402, in turn, is based upon and claims the benefit under 35 U.S.C. §119(e) of the following U.S. provisional patent applications: Ser. No. 60/427,908, filed Nov. 19, 2002, and Ser. No. 60/512,136, filed Oct. 17, 2003.

U.S. patent application Ser. No. 10/734,017, in turn, is based upon and claims the benefit under 35 U.S.C. §119(e) of U.S. Provisional Patent Application Ser. No. 60/454,217, filed Mar. 12, 2003.

U.S. patent application Ser. No. 10/873,522, in turn, is based upon and claims the benefit under 35 U.S.C. §119(e) of U.S. Provisional Patent Application Ser. No. 60/480,529, filed Jun. 20, 2003.

U.S. patent application Ser. No. 10/993,205, in turn, is based upon and claims the benefit under 35 U.S.C. §119(e) of U.S. Provisional Patent Application Ser. No. 60/541,414, filed Feb. 2, 2004.

U.S. patent application Ser. No. 11/109,984, in turn, is based upon and claims the benefit under 35 U.S.C. §119(e) of U.S. Provisional Patent Application Ser. No. 60/563,860, filed Apr. 19, 2004.

U.S. patent application Ser. No. 11/109,985, in turn, is based upon and claims the benefit under 35 U.S.C. §119(e) of U.S. Provisional Patent Application Ser. No. 60/563,767, filed Apr. 19, 2004.

U.S. patent application Ser. No. 11/112,858, in turn, is based upon and claims the benefit under 35 U.S.C. §119(e) of U.S. Provisional Patent Application Ser. No. 60/564,853, filed Apr. 22, 2004.

U.S. patent application Ser. No. 11/273,811, in turn, is based upon and claims the benefit under 35 U.S.C. §119(e) of U.S. Provisional Patent Application Ser. No. 60/627,297, filed Nov. 12, 2004.

U.S. patent application Ser. No. 11/274,597, in turn, is based upon and claims the benefit under 35 U.S.C. §119(e) of U.S. Provisional Patent Application Ser. No. 60/627,721, filed Nov. 12, 2004.

U.S. patent application Ser. No. 11/449,554, in turn, is a continuation of U.S. patent application Ser. No. 10/873,522, now U.S. Pat. No. 7,537,596, which, in turn, is based upon and claims the benefit under 35 U.S.C. §119(e) of U.S. Provisional patent application Ser. No. 60/480,529, filed Jun. 20, 2003.

U.S. patent application Ser. No. 11/486,959, in turn, is based upon and claims the benefit under 35 U.S.C. §119(e) of U.S. Provisional Patent Application Ser. No. 60/699,277, filed Jul. 13, 2005.

U.S. patent application Ser. No. 11/585,378, in turn, is based upon and claims the benefit under 35 U.S.C. §119(e) of U.S. Provisional Patent Application Ser. No. 60/729,373, filed Oct. 21, 2005.

U.S. patent application Ser. No. 11/929,026, in turn, is based upon and claims the benefit under 35 U.S.C. §119(e) of U.S. Provisional Patent Application Ser. No. 60/856,128, filed Nov. 1, 2006.

U.S. patent application Ser. No. 12/175,223, in turn, is based upon and claims the benefit under 35 U.S.C. §119(e) of U.S. Provisional Patent Application Ser. No. 60/961,317, filed Jul. 19, 2007.

U.S. patent application Ser. No. 12/176,913, in turn, is based upon and claims the benefit under 35 U.S.C. §119(e) of U.S. Provisional Patent Application Ser. No. 60/961,317, filed Jul. 19, 2007.

U.S. patent application Ser. No. 13/246,687, in turn, is based upon and claims the benefit under 35 U.S.C. §119(e) of U.S. Provisional Patent Application Ser. No. 61/390,121, filed Oct. 5, 2010.

U.S. patent application Ser. No. 13/246,690, in turn, is based upon and claims the benefit under 35 U.S.C. §119(e) of U.S. Provisional Patent Application Ser. No. 61/386,921, filed Sep. 27, 2010.

U.S. patent application Ser. No. 13/246,684, in turn, is based upon and claims the benefit under 35 U.S.C. §119(e) of U.S. Provisional Patent Application Ser. No. 61/386,925, filed Sep. 27, 2010.

Each of these priority patent applications is incorporated herein by reference in its entirety for all purposes.

INTRODUCTION

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bones that become fractured should be repaired promptly and properly. Typically, a fractured bone is treated using a fixation device, which reinforces the fractured bone and keeps it aligned during healing. Fixation devices may take a variety of forms, including casts or fixators for external fixation, and bone plates and/or fasteners (screws, pins, wires, etc.), for internal fixation, among others.

Bone plates are sturdy internal devices, usually made of metal, that mount directly to the bone adjacent a fracture (or other bone discontinuity). To use a bone plate to repair a discontinuity of a bone, a surgeon typically (1) selects an appropriate plate, (2) reduces the discontinuity (e.g., sets the fracture), and (3) fastens the plate to bone fragments disposed on opposing sides of the discontinuity using suitable fasteners, such as screws and/or wires, so that the bone plate spans the discontinuity and the bone fragments are fixed in position.

Bone plates generally include a plurality of apertures configured to receive fasteners such as bone screws. An aperture may have a circular or elongate (e.g., oval) shape, according to its intended use.

Elongate apertures may be suitable for longitudinal adjustment of bone fragments relative to a bone plate. In particular, the bone plate may be coupled to bone using bone screws placed through one or more elongate apertures of the plate, but with the bone screws not seated fully against the plate. The position of the bone screws and attached bone fragments then may be adjusted along the long axis of the apertures before and/or as the bone screws are tightened fully against the bone plate. Accordingly, bone fragments may be compressed together longitudinally, to reduce any gap between the fragments, thereby promoting callous formation and decreasing the chance of a chronic nonunion at a fracture site.

In some examples, the elongate apertures may have wall surfaces that are sloped longitudinally, to promote a camming action ("camming apertures"). An exemplary structure and operation of a camming aperture is shown in U.S. Pat. No. 4,513,744 to Klaue, which is incorporated herein by reference. In use, rotational advancement of a semi-spherical head of the bone screw against a sloped wall of the camming aperture causes the bone screw to move longitudinally along the aperture. Accordingly, a bone screw may be placed, initially, toward the end of the aperture that is farther from the fracture, and then tightened so that the bone screw and its attached bone fragment move toward an adjacent bone fragment, to provide dynamic compression of the bone.

Apertures of a bone plate also may be locking or nonlocking. A locking aperture may engage a bone screw (e.g., via a thread) so that the bone screw is attached directly to the bone plate, to restrict translational motion of the bone screw in both directions along the long axis of the bone screw. In contrast, a nonlocking aperture does not attach a bone screw directly to the bone plate. Instead, the nonlocking aperture relies on the ability of bone to hold the bone screw such that the head of the bone screw bears against the outer surface of the plate, thus holding the plate against the bone.

Locking apertures may have a number of advantages over nonlocking apertures. These advantages may include (1) less plate slippage, (2) less damaging contact between the bone plate and bone, (3) reduced dependence on bone quality for fixation, and/or (4) a reduced tendency for bone screws to loosen and/or back out. Accordingly, locking apertures may offer increased blood flow, less damage to the periosteum, improved callous formation, and/or a small, and sometimes desirable, increase in flexibility of the fixed bone.

Standard locking apertures are circular. These locking apertures thus do not offer the capability to compress bone longitudinally during plate installation. Accordingly, the advantages of locking apertures may be offset by improper reduction, for example, an excessive gap between bone fragments during fixation.

SUMMARY

The present teachings provide a system, including methods, apparatus, and kits, for fixing bones with bone plates having movable locking elements.

BRIEF DESCRIPTION OF THE DRAWINGS

FIG. 4 is a fragmentary, longitudinal sectional view of the system of FIG. 1, taken during an exemplary installation of the bone plate on bone, particularly with a bone screw disposed in the elongate locking aperture but not fully seated in the locking aperture, in accordance with aspects of the present teachings.

FIG. 5 is a fragmentary, longitudinal sectional view of the system of FIG. 1, taken generally as in FIG. 4, but after the bone screw has been fully advanced and seated in the locking aperture to compress the bone, in accordance with aspects of the present teachings.

FIG. 6 is a fragmentary, longitudinal sectional view of another exemplary fixation system including a bone plate having an elongate locking aperture and connected to bone via a bone screw disposed in threaded engagement with a locking element of the locking aperture, with the bone screw in a partially advanced configuration, in accordance with aspects the present teachings.

FIG. 7 is a fragmentary, longitudinal sectional view of the fixation system of FIG. 6, taken generally as in FIG. 6, with the bone screw pivoted to an oblique angle relative to the bone plate, in accordance with aspects of the present teachings.

FIG. 8 is a fragmentary, transverse sectional view of an exemplary fixation system including a bone plate having a locking aperture with a biased locking element, with the bone plate disposed on bone and receiving a bone screw that is being rotated against a countersink surface of the locking aperture, in accordance with aspects of the present teachings.

FIG. 9 is a sectional view of the fixation system of FIG. 8, taken generally as in FIG. 8, after the bone screw has been rotated against the countersink surface of the locking aperture to pull the biased locking element toward the countersink surface, to provide compression of the bone plate against bone, in accordance with aspects of the present teachings.

FIG. 10 is an exploded view of an exemplary bone plate having elongate locking apertures, in accordance with aspects of the present teachings.

FIG. 11 is a sectional view of the bone plate of FIG. 10 in an assembled configuration, taken generally along line 11-11 of FIG. 10.

FIG. 12 is a bottom view of the bone plate of FIG. 10 with the bone plate in the assembled configuration of FIG. 11.

FIG. 13 is a bottom view of another exemplary bone plate having an elongate locking aperture, in accordance with aspects of the present teachings.

FIGS. 14 and 15 are sectional views of the bone plate of FIG. 13, taken generally along line 15-15 of FIG. 13 during (FIG. 14) and after (FIG. 15) an exemplary installation of a locking element to create the locking aperture, in accordance with aspects of the present teachings.

FIG. 16 is a pair of transverse sectional views of still another exemplary bone plate with an elongate locking aperture, taken through the locking aperture in respective exploded and assembled configurations, to illustrate another exemplary strategy for constructing a locking aperture, in accordance with aspects of the present teachings.

FIG. 17 is a pair of bottom views of still yet another exemplary bone plate having an elongate locking aperture, shown as respective exploded and assembled configurations of the locking aperture, to illustrate yet another exemplary strategy for constructing a bone plate having an elongate locking aperture, in accordance with aspects of the present teachings.

FIG. 18 is a side view of an exemplary bone plate having a plurality of locking elements hooked onto a plate body of the bone plate to provide a pair of elongate locking apertures, with one of the locking elements being advanced onto the plate body and thus disposed out of alignment with a corresponding elongate opening of the plate body, in accordance with aspects of the present teachings.

FIG. 19 is a fragmentary, sectional view of the bone plate of FIG. 18, taken generally along line 19-19 of FIG. 18 through a locking aperture of the bone plate.

DETAILED DESCRIPTION

Figure 1:
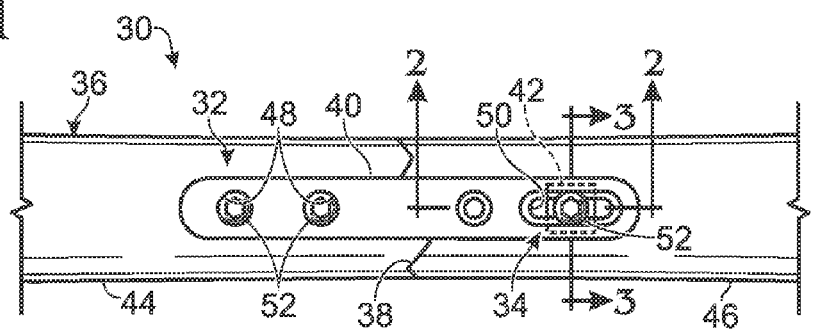
FIG. 1 is a plan view of an exemplary system for fixing bones, with the system including a bone plate secured to a fractured bone and composed of a plate body connected to a movable locking element to create an elongate locking aperture, in accordance with aspects of present teachings.

The present teachings provide a system, including methods, apparatus, and kits, for fixing bones with bone plates having movable locking elements.

Each bone plate may include (1) a plate body defining one or more body openings, particularly body openings that are elongate (oblong), and (2) one or more locking elements. Each locking element may define a through-hole(s) for receiving a threaded region of a fastener in threaded engagement with the locking element (i.e., in a locked configuration). Accordingly, the through-hole(s) of the locking element may be aligned with a body opening, such that the body opening and the through-hole of the locking element collectively form a locking aperture of the bone plate for receiving threaded fasteners, such as bone screws.

The locking element may be connected movably to the plate body. For example, the locking element may be slidable along a long axis of the body opening (e.g., if the body is configured as a compression opening with a sloped countersink wall). Sliding motion of the locking element may permit repositioning the fastener (and an associated bone fragment) with the fastener locked to the bone plate, to provide compression of bone. Alternatively, or in addition, the locking element may be movable/deformable (1) angularly to permit placement of the fastener at a range of angles and/or (2) in a direction normal to an adjacent bone surface to provide compression of the bone plate against bone. In some examples, the locking element may include a biasing mechanism that biases the position of the locking element (and/or a through-hole thereof) in relation to the plate body (e.g., biased along a thickness axis of the plate body).

The locking element may be connected to the plate body in the absence of a fastener that locks to the locking element and/or may be connected via the fastener. In any case, the locking element may have any suitable position relative to the plate body, such as being disposed partially, substantially, at least mostly, or completely internal to the plate body (e.g., in a cavity defined by the plate body); disposed at least substantially externally on the plate body (e.g., being hooked onto the plate body); and/or abutted with/projecting from the plate body (such as projecting from an inner face of the plate body to space the plate body from bone).

The systems of the present teachings may provide substantial advantages in bone fixation. For example, the systems may provide longitudinal compression of bone with bone plates and locked fasteners, more controlled compression of bone plates against bone, and/or placement of locking fasteners at a range of angles, among others. Injured bones thus may heal at an accelerated rate and/or with an improved outcome.

The following sections describe further aspects of the present teachings, including, among others, (I) an overview of exemplary fixation systems, (II) bone plates, (III) fasteners, (IV) methods of fixing bones using bone plates with movable locking elements, and (V) examples.

I. Overview of Exemplary Fixation Systems

FIG. 1 shows an exemplary system 30 for fixing bones. The system may include a bone plate 32 with an elongate locking aperture 34. The bone plate may be secured to a bone 36 having a discontinuity, such as a fracture 38. The bone plate may be composed of a plate body 40 connected to a movable locking element 42, to create locking aperture 34. The plate body may be structured to span the fracture, for example, extending longitudinally on bone 36 between bone fragments 44, 46.

The plate body may define a plurality of openings 48, including an elongate opening 50 for receiving fasteners 52, particularly threaded fasteners such as bone screws. (Here, one of the openings lacks a fastener.) The fasteners may extend through openings 48 and into bone, thereby securing the bone plate to the bone. Furthermore, elongate opening 50 and locking element 42 may cooperate to collectively create locking aperture 34 of the bone plate.

Figure 2:
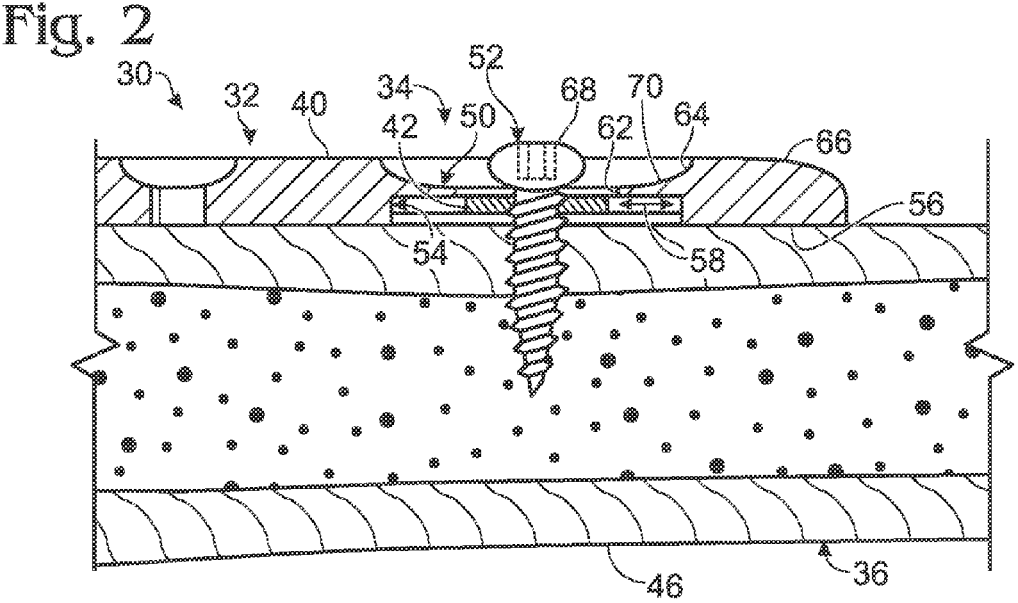
FIG. 2 is a longitudinal sectional view of the system of FIG. 1, taken generally along line 2-2 of FIG. 1 through the elongate locking aperture.

FIG. 2 shows a longitudinal sectional view of system 30 taken through locking aperture 34 of the bone plate. Locking aperture 34 may have locking element 42 disposed below opening 50 (i.e., inward of the opening and closer to bone). For example, plate body 40 may define a cavity 54 extending into the plate body from an inner face 56 of the plate body. Locking element 42 may be disposed in cavity 54 and slidable along the cavity, particularly, slidable parallel, indicated at 58, to a long axis defined by opening 50.

Opening 50 of the plate body may adjoin cavity 54. The opening may include a through-hole region 62 and a countersink 64 disposed in respective adjacent and spaced positions relative to cavity 54. In particular, the countersink may be defined as a recessed region in an outer face 66 of the plate body. The countersink may be sized to at least partially receive a head 68 of bone screw 52. In addition, the countersink may provide an inclined (sloped) countersink surface or ramp 70 that offers a camming action as head 68 is turned against the countersink surface.

Figure 3:
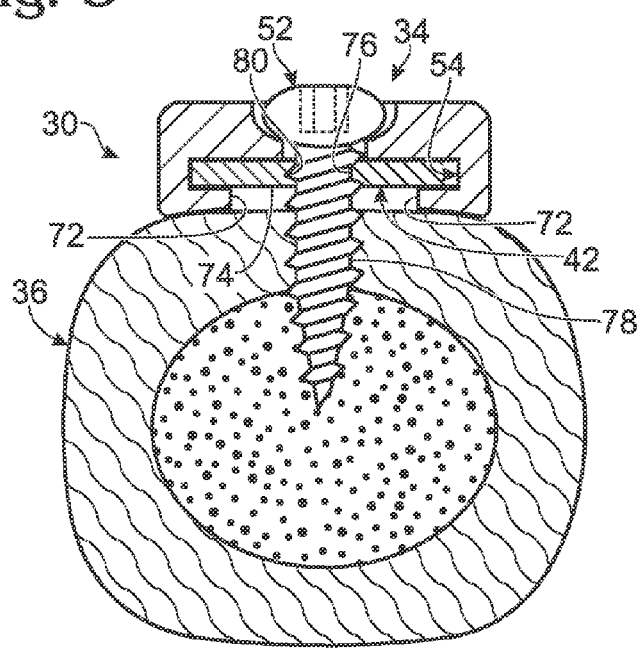
FIG. 3 is a transverse sectional view of the system of FIG. 1, taken generally along line 3-3 of FIG. 1.

FIG. 3 shows a transverse sectional view of system 30 taken through elongate locking aperture 34 of the bone plate. Locking element 42 may be retained in cavity 54 of the plate body by one or more flanges or ledges 72 projecting into the cavity, for example, as shown here, projecting toward one another transversely from opposing lateral sides of the cavity. The flanges or other support structure of the plate body thus may provide an inner wall that engages and supports the locking element when the inner face of the plate body is facing downward. The inner wall (and/or an outer wall in some cases) thus may restrict separation of the locking element from the plate body. The locking element may be spaced from bone, such as having an inner surface 74 that is recessed from the inner face of the plate body, as shown here. Alternatively, the locking element may be flush with the inner face of the plate body, or may extend over and/or project from the inner face of the plate body, to position at least a portion of the locking element closer to bone than the plate body (e.g., see Example 3). In these embodiments, the locking element may engage the bone surface or may be spaced from the bone surface, such as being pulled away from the bone surface as the plate body is compressed against bone by the fastener (e.g., see Examples 2 and 5, among others).

Locking element 42 may define a through-hole 76 for receiving a threaded shank 78 of fastener 52. A wall of the through-hole may be configured to engage the threaded shank such that the fastener is locked to (e.g., disposed in threaded engagement with), the locking element. "Locked" or "lock," as used herein in relation to a fastener, means that translational movement of the fastener is restricted for both opposing axial directions of the fastener. (However, advancement and/or retraction of the fastener may be permitted by turning the fastener.) In addition, "threaded engagement," as used herein in relation to a fastener, means that a threaded region of the fastener (and/or of a locking element) is engaged with a counterpart structure of the locking element (and/or fastener) to lock the fastener to the locking element. The wall of through-hole 76 thus may define an internal thread 80 (and/or a short segment(s) thereof), or other preformed structure (such as a lip(s)/tab(s)), that is configured to engage the external thread of the threaded shank. Alternatively, or in addition, the wall of through-hole 76 may be configured to be deformed by the threaded shank as the fastener is advanced through the opening rotationally. Through-hole 76 thus may be undersized in relation to the diameter of the shank.

FIGS. 4 and 5 collectively show fixation system 30 providing compression of bone 36 as bone screw 52 is advanced from an initial partially seated configuration (FIG. 4) to a more fully seated configuration (FIG. 5) in locking aperture 34.

FIG. 4 shows bone plate 32 secured to bone fragments 44, 46 disposed on opposing sides of fracture 38, such that the bone plate spans the fracture. Bone screw 52 may be disposed in locking aperture 34 with locking element 42 positioned toward a distal end of the locking aperture. In particular, the bone screw may extend through elongate opening 50 of the plate body, through through-hole 76, and into bone 36 (e.g., unicortically, as shown here, or bicortically). Head 68 of the bone screw may be engaged with ramp surface 70 of the countersink. Additional rotational advancement of the bone screw, indicated at 90, via a driver may urge the head of the bone screw along the ramp surface, providing net longitudinal movement of the bone screw in a direction, indicated at 92, generally parallel to the long axis of elongate opening 50 (and also parallel to the long axis of the elongate locking aperture). Longitudinal movement of the bone screw may generate corresponding movement of the locking element and engaged bone (namely, bone fragment 46).

FIG. 5 shows system 30 with bone 36 compressed. In particular, bone fragments 44, 46 may be abutted against one another, indicated at 94, relative to the gapped configuration prior to compression (compare FIGS. 4 and 5). Here, head 68 of the bone screw has traveled to a final or more stably seated position that is more central to opening 50. Generally, the final position may be a nonsloped and/or less-sloped position at or near an end and/or transition point of the ramp surface of the countersink. Alternatively, the seated position to which the bone screw is advanced may be determined by abutment of bone fragments against one another, to restrict further longitudinal movement of the bone screw and its attached bone fragment(s).

II. Bone Plates

Bone plates including an assembly of a plate body and one or more locking elements generally comprise any relatively low-profile (or plate-like) fixation device configured to stabilize at least one bone by attachment to the bone. The fixation device may be configured to span any suitable bone discontinuity (or discontinuities) so that the fixation device fixes the relative positions of bone portions/fragments (and/or bones) disposed on opposing sides of the bone discontinuity (or discontinuities). Alternatively, or in addition, the fixation device may reinforce a bone lacking a discontinuity.

Suitable discontinuities may occur naturally and/or may result from injury, disease, and/or surgical intervention, among others. Accordingly, exemplary discontinuities for use with the fixation devices described herein may include joints, fractures (breaks in bones), osteotomies (cuts in bones), and/or nonunions (for example, produced by injury, disease, or a birth defect), among others.

The bone plates described herein may be configured for use on any suitable bone, in any suitable species, including human, equine, canine, and/or feline species, among others. Exemplary bones may include bones of the arms (radius, ulna, humerus), legs (femur, tibia, fibula, patella), hands/wrists (e.g., phalanges, metacarpals, and carpals), feet/ankles (e.g., phalanges, metatarsals, and tarsals), vertebrae, scapulas, pelvic bones, cranial bones, facial bones, the ribs, the sternum, and/or clavicles, among others.

Each bone plate may be an internal fixation device configured to be disposed at least mostly or completely internally during fixation. The bone plate thus may be disposed at least substantially or completely under the skin of a plate recipient after installation, generally such that the bone plate is apposed to and/or in contact with the bone. The installed bone plate thus may overlie bone and underlie soft tissue.

Each bone plate may be configured to be disposed in any suitable exterior/interior position relative to its target bone. The bone plate (or a plate portion) may be configured to be disposed in contact with an exterior surface of the bone and thus may be positioned at least substantially (or completely) exterior to the bone. Alternatively, the bone plate may be configured to be disposed at least partially interior to a bone, that is, apposed to (normally) interior bone surfaces when secured to the bone. The interior surfaces of the bone may be accessed during installation of the bone plate (such as by punching the bone plate through the exterior bone surface) and/or may be accessible due to a break, a cut, and/or the like.

The bone plates may be formed of any suitable material(s). These materials may provide the bone plate with a sturdy yet malleable construction. Generally, the bone plates should be stiffer and stronger than the section of bone spanned by the plates, yet flexible (e.g., springy) enough not to strain the bone significantly. Suitable materials for forming the bone plates may include metal, polymer, plastic, ceramic, composite, bone material, and/or the like. Suitable materials may include biocompatible materials. Exemplary biocompatible materials may include metals/metal alloys (for example, titanium or titanium alloys; alloys with cobalt, chromium, and/or molybdenum; stainless steel; etc.), biocompatible plastics (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)), and/or bioresorbable materials (such as polygalactic acid (PGA), polylactic acid (PLA), polycaprolactones, copolymers thereof, etc.), among others.

The bone plates may be configured to reduce irritation to the bone and surrounding tissue. For example, the bone plates may be formed of a biocompatible material, as described above. In addition, the bone plates may have a low and/or feathered profile to reduce their protrusion into adjacent tissue and rounded, burr-free surfaces to reduce the effects of such protrusion.

The bone plates may be sized and shaped to conform to particular portions of a bone (or bones). The plates may be generally elongate, with a length L, a width W, and a thickness T. Here, length L ≥width W>thickness T. In use, the long axis of the bone plates (or of a plate body) may be aligned with the long axis of the corresponding bone, and/or may extend obliquely and/or transversely relative to the bone's long axis. The length and/or width of the bone plates may be varied according to the intended use, for example, to match the plates with a preselected region of bone(s) and/or a particular injury to the bone. For example, the plates may be generally linear for use on the shaft of a long bone and/or may have a nonlinear shape, such as for use near an end of a bone and/or for transverse placement on the shaft, among others. In some embodiments, the bone plates may be configured for use on both sides of the body/skeleton, such as when the bone plates (and/or plate bodies) are bilaterally symmetrical. In some embodiments, the bone plates (and/or plate bodies) may be asymmetrical, such that each bone plate is configured for use on either the left or the right side of the body/skeleton, but not both.

The bone plates may include inner (bone-facing) and outer (bone-opposing) faces (and/or surfaces). In some examples, a plate body of each bone plate may provide the outer face, and one or locking elements may provide at least a portion of the inner face. One or both of these faces may be contoured generally to follow an exterior surface of a target bone (or bones) for which a bone plate is intended, so that the bone plate maintains a low profile and fits onto the bone(s). For example, the inner face of a bone plate may be generally complementary in contour to the bone surface, such as being concave to fit onto a convex bone surface. The outer face of the plate also may correspond in contour to the bone surface and may be generally complementary to the inner face of the plate, maybe planar, and/or the like. The bone plates may be partially and/or completely precontoured, at the time of manufacture, allowing practitioners to apply them to bone(s) with little or no additional bending at the time of application. The bone plates thus may serve as templates for reconstructing damaged bones. Alternatively, or in addition, the bone plates may be custom-contoured by practitioners before and/or during installation onto bone.

The thickness of the bone plates may be defined by the distance between the inner and outer faces of the plates. The thickness of the plates may vary between plates and/or within the plates, according to the intended use. For example, thinner plates may be configured for use on smaller bones and/or on bones or bone regions where soft tissue irritation is a greater concern. Thickness may vary within the plates. For example, the plates may become thinner as they extend over protrusions (such as processes, condyles, tuberosities, and/or the like), reducing their profile and/or rigidity, among others. The thickness of the plates also may be varied to facilitate use, for example, to make the plates thinner where they typically need to be deformed by bending and/or twisting the plates, such as at a junction (or bridge region) between plate portions. In this way, the plates may be thicker and thus stronger in regions where they may not need to be contoured, such as along the shaft of the bone. In some embodiments, the thickness of the plates may be determined, at least in part, by the thickness and position of the locking elements in the bone plates. For example, thicker locking elements may give rise to thicker bone plates (contributing substantially to the overall thickness of the plates) and thinner locking elements may, in some cases, enable the bone plates to be thinner. Furthermore, the position of the locking elements relative to the plate bodies may determine, at least partially, how the locking elements contribute to the thickness of the bone plates.

The bone plates may include one or more projections. The projections may extend, for example, generally orthogonal from the inner face of the bone plates toward bone. Alternatively, or in addition, the projections may extend generally outward from the outer surface of the bone plates. The projections may be sharp or blunt according to their intended use. For examples, sharp projections may be configured as prongs that penetrate bone to restrict movement of the bone plates. Prongs may be used in place of, or in addition to, bone fasteners, for one or more portions of each bone plate (and/or plate body). Blunt (or sharp) projections, such as ridges or knobs, may be configured to elevate the inner surface of the bone plates (and/or plate bodies) from the bone surface, for example, to allow space for tissue between the plates and bone and/or to decrease the effective stiffness of the bone plate.

The bone plates of the present teachings may include a plurality of discrete components, including at least one plate body and one or more locking elements, to create one or more locking apertures. Each locking element can be coupled to the plate member before placement of a threaded fastener into the corresponding elongate locking aperture (e.g., see Examples 1 and 2) and/or can be coupled by placement of a threaded fastener into the aperture. Further aspects of bone plates are described in the following subsections, including (A) plate bodies, and (B) locking elements.

A. Plate Bodies

A plate body, as used herein, may include any of the structures, features, or properties described above for bone plates. In particular, the plate body may be a major portion of the bone plate, that is, a major determinant of the overall size and/or shape of the bone plate. Accordingly, the plate body may have, at least substantially, the characteristic dimensions (e.g., the length, width, and/or thickness), shape, strength, flexibility, number of openings for receiving fasteners, surface features, and/or the like, of a corresponding bone plate in which the plate body is included.

The plate body generally includes a plurality of openings. The openings may be adapted to receive fasteners for securing the plate body to bone. Alternatively, or in addition, one or more of the openings may be configured to receive a locking element(s), to alter the local rigidity of the plate body, to permit the plate body to be manipulated with a tool (such as an attachable handle), to facilitate blood flow to bone regions where the plate body is installed, to promote healing, and/or the like.

The openings may have any suitable positions, sizes, and/or arrangement within each portion of a plate body. The openings (or any suitable subset thereof) may be arrayed generally in a line along the plate body (or an anchor portion thereof), for example, centered across the width of the plate body. Alternatively, the apertures may be arranged nonlinearly, for example, disposed in an arcuate, staggered, or other two-dimensional (or three-dimensional) arrangement.

The openings may have any suitable shape and structure. Generally, the openings may be non-elongate (e.g., circular or square, among others) or elongate/oblong (such as oval, elliptical, rectangular, etc.). The openings may include countersinks (also termed counterbores). The countersinks may be configured, for example, to receive a head of a fastener, to reduce or eliminate protrusion of the head above the outer surface of the plate body. Each opening may be threaded or nonthreaded, and each plate body may include one or more threaded and/or nonthreaded openings. In some embodiments, the plate member may include one or a plurality of elongate openings (for example, oval apertures) extending parallel, obliquely, and/or transversely relative to the long axis of each plate body. The elongate openings may be compression slots that include sloped countersink walls to provide compression when heads of fasteners are advanced against the sloped walls. Alternatively, or in addition, the elongate openings may be used to adjust the position of the plate body and/or anchor portions within the plate body relative to bone before the plate body is fully secured to the bone.

The plate body may have at least one, and generally two or more, anchor portions configured to be secured to different regions of a bone (or bones). Each anchor portion may be structured for a specific region of a bone. For example, the plate body may include a proximal anchor portion for attachment to a more proximal region of a bone, and a distal anchor portion for attachment to a more distal region of the same bone. Alternatively, or in addition, the plate body may include an exterior anchor portion configured to fit against an exterior surface region of bone adjacent a bone discontinuity, and/or an interior anchor portion configured to be received in an interior (e.g., recessed, resected, and/or excavated) region of bone adjacent the bone discontinuity.

The anchor portions of a plate body may have any suitable connection. In some examples, the anchor portions may be formed unitarily, such that a monolithic plate body includes the anchor portions. Alternatively, anchor portions may be formed as separate pieces. The separate pieces may be connected by any suitable connection and/or joint, including a fastener(s), welding, a hinge joint, a ball-and-socket joint, and/or the like. Further aspects of plate bodies having adjustable joints are described in the following patent application, which is incorporated herein by reference: U.S. patent application Ser. No. 10/716,719, filed Nov. 19, 2003.

The anchor portions of a plate body may have any suitable relative disposition. The anchor portions may be disposed such that they are substantially collinear and/or parallel, oblique, or substantially transverse to one another. The relative disposition may be fixed and/or adjustable. In some examples, the anchor portions may be connected unitarily by a deformable bridge region, so that the plate body can be bent pre- and/or peri-operatively to adjust the relative disposition of the anchor portions. Alternatively, the anchor portions may be distinct pieces connected, for example, through an adjustable joint, as described above.

Each anchor portion may have one or more openings and/or other receiving structures. Each opening (or a subset of the openings) may be configured to receive a fastener that extends into bone.

The plate body may have any suitable receiver structure(s) for receiving the locking elements. Each receiver structure may be configured such that a locking element is received, at least partially, in or over the receiver structure. Accordingly, the receiver structure may be in the form of an opening (a "receiver opening") such as a cavity or recess, among others. The receiver opening may be defined by any suitable surface (s) of the plate body, such as the inner face/surface, one or both opposing lateral/side surfaces, and/or the outer face/surface. Alternatively, or in addition, the receiver structure may be or may include a projection(s), such as a tab(s), flange(s), ridge(s), etc., and may be formed by any suitable surface of the bone plate, that is, any of the surfaces listed below for the receiver openings. In some examples, the plate body may lack a receiver structure, for example, if the locking element is connected to the plate body only by a fastener that locks to the locking element.

The receiver opening may have any suitable structure. The receiver opening may or may not communicate with (may or may not be contiguous with) one or more elongate openings (for receiving fasteners) of the plate body, generally based on where the receiver opening is formed on the plate body. The receiver opening may be a single cavity that is sized and/or otherwise configured to receive only one locking element or to receive a plurality of locking elements.

Each characteristic dimension of the receiver opening may be less than, about the same as (or only slightly greater than), or substantially greater than an aligned dimension of the locking element. In some examples, the axial dimension of the receiver opening (generally its length), measured parallel to the long axis of a corresponding elongate opening and/or of the plate body, may be substantially greater than the corresponding dimension of the locking element, to allow the locking element to slide axially along the elongate opening and/or plate body. Alternatively, the axial dimension of the receiver opening may be less than the corresponding dimension of the locking element if the locking element is received only partially in the receiver structure. In addition, a first transverse dimension of the receiver opening (generally its width), measured parallel to a width axis of the plate body with the bone plate assembled, may be slightly larger than the corresponding dimension of the locking element. The first transverse dimension may allow the locking element to be received in the receiver opening, and to slide axially within the receiver opening, but not substantially from side to side relative to the plate member, so that an opening of the locking element remains centered transversely in relation to an overlying elongate opening(s) of the plate body. Alternatively, the first transverse dimension of the receiver opening may be less than the corresponding dimension of the locking element, for example, if the receiver opening(s) is formed on the sides and/or outer face of the plate body, and/or if the receiver opening is formed on the inner face of the plate body such that the locking element can be received only partially (or not at all) in the receiver opening. Furthermore, a second transverse dimension of the receiver opening (generally its thickness or depth), measured parallel to the thickness axis of the plate body, may be greater than, about the same as, or less than, the corresponding dimension of the locking element. If greater than the corresponding dimension, the locking element may be spaced from the inner surface of the plate member (and, generally, bone) with the bone plate installed and/or may be capable of pivotable movement to an oblique orientation (e.g., see Examples 1 and 2). If about the same as the corresponding dimension, the locking element may be flush with the inner face of the plate body. If less than the corresponding dimension, the locking element may protrude from the inner face of the plate body toward bone, such that the locking element contacts bone and spaces the plate body (at least locally) from bone, with the bone plate installed on bone.

The receiver opening may be shaped to retain the locking element after the locking element is received in the receiver opening, such that the locking element is connected to the plate member. For example, the receiver opening may be shaped such that the locking element can slide axially but not substantially from side-to-side. Accordingly, an inner wall(s) (and/or outer wall(s)) of the plate body, such as a flange(s), may restrict separation of the locking element from the plate body.

The receiver opening may be configured to receive the locking element at any suitable position(s) within the plate member. For example, the receiver opening may extend at least substantially to one end or to opposing ends of the plate body, so that the locking element can enter the receiver opening longitudinally from one or both of the ends. Alternatively, or in addition, the receiver opening may be positioned and structured to receive the locking element at one or more intermediate positions along the plate body. In some examples, the locking element may be received transversely and then slid longitudinally to a position(s) (e.g., to be held by a flange(s) or tab(s), among others) at which transverse motion of the locking element is restricted.

In some embodiments, the receiver structure may be configured such that a locking element is received over the receiver structure. For example, the receiver structure may include a recess(es) and/or projection(s) formed on the inner face, sides, and/or outer face of the plate body. In some examples, the recess(es) and/or projection(s) may extend longitudinally on the plate body for the entire length of the plate body and/or a portion thereof (e.g., see Example 5).

B. Locking Elements

Each bone plate of the present teachings may include one or more locking elements. Each locking element may be positioned or positionable in alignment with one or more openings of the plate body, such that a threaded fastener can be placed from an opening, through the locking element, and into bone.

Each locking element may include a through-hole (or two more through-holes) for receiving a threaded fastener(s). The through-hole may have a circumferential wall extending only partially or extending completely around the through-hole. Furthermore, the locking element may include structure for engagement of a threaded region of the fastener(s) (e.g., a portion of the fastener's shank), to lock the fastener(s) to the locking element. The engagement structure generally may be provided by a wall of the through-hole, and may include an internal thread or a thread-like feature (corresponding to, and/or functioning like, one or more partial or complete segments of a thread). The thread or thread-like feature may allow threaded engagement (and, generally, rotational advancement/retraction) of the threaded fastener with (and with respect to) the locking element. In some embodiments, the locking element, at least initially, may lack a preformed thread or thread-like structure. However, the structure (e.g., diameter) of the through-hole and composition of the locking element may be selected such that the thread of the threaded fastener deforms the opening of the locking element, as the fastener is advanced into the opening, to lock the fastener to the locking element, such as via a friction fit or friction weld, among others. Accordingly, in some examples, the locking element may be formed of a material that is softer and/or more malleable than a corresponding fastener and/or plate body.

Each locking element may include any suitable internal thread. Generally, the internal thread may be selected according to a threaded fastener to be placed through the locking element. In particular, the pitch of the internal thread may be about the same as the pitch of an external thread on a threaded shank of the fastener. In some embodiments, the locking element may be constructed to be thinner when used with a fastener having a lesser thread pitch and constructed to be thicker when used with a fastener having a greater thread pitch, to achieve engagement in each case between the same number of thread segments.

Each locking element may include and/or may be formed at least substantially of any suitable material(s). Exemplary materials that may be suitable generally are biocompatible and/or bioresorbable, for example, any of the materials listed above in relation to bone plates. The locking element may be formed of the same material as the plate member or of a different material. For example, both the locking element(s) and plate member may be formed of the same or different metals/metal alloys or the locking element may be formed of plastic and/or a bioresorbable material and the plate member may be formed of metal, or vice versa, among others. Furthermore, the material and/or dimensions of each locking member may be selected such that the locking member is relatively rigid, such that the locking member does not flex substantially during normal use of the bone plate, or relatively flexible, such that locking member does flex substantially during normal installation and/or use of the bone plate.

The locking elements of a bone plate may be substantially the same in size, shape, etc., or may have distinct properties. For example, the locking elements may have different sizes of openings, may be of different thickness, may be formed of different material, may have distinct thread pitches, and/or the like.

The locking element(s) of a bone plate may be supplied in an assembled or non-assembled configuration with a plate body of the bone plate. If assembled, the locking element(s) may be configured to be removable or nonremovable. If non-assembled, the locking element(s) may be assembled with the plate body before and/or during installation of the plate member on bone. In some examples, assembly may involve deforming a region of the plate body and/or installing an ancillary fastener (such as a screw or clip, among others), to restrict removal of the locking element. In some examples, assembly may involve assembling a plate body with a locking element via a fastener extending through the plate body and locked to the locking element.

III. Fasteners

Fasteners suitable for use with the bone plates of the present teachings generally comprise any mechanism for affixing a bone plate to a bone, including screws, pins, and/or wires, among others. Bone screws may include unicortical, bicortical, and/or cancellous bone screws. Unicortical and bicortical bone screws typically have relatively small threads for use in hard bone, such as is typically found in the shaft portion of a bone, whereas cancellous bone screws typically have relatively larger threads for use in soft bone, such as is typically found near the ends (metaphyseal regions) of a long bone. Unicortical bone screws penetrate the bone cortex once, adjacent the bone plate, whereas bicortical bone screws penetrate the bone cortex twice, once adjacent the bone plate and again opposite the bone plate. Generally, unicortical screws provide less support than bicortical screws, because they penetrate less cortex. The size and shape of the fasteners may be selected based on the size, shape, and/or position of underlying bone, and/or based on the structure of a locking or nonlocking aperture into which each fastener is to be placed.

Each fastener placed in a locking aperture may have a threaded shank. The threaded shank may have one thread (single-threaded) or a plurality of threads (e.g., double-threaded, triple-threaded, etc.). The threads may be interspersed, so that the shank is multi-threaded, for example, to accommodate a greater pitch (a steeper thread angle). Alternatively, or in addition, discrete threaded regions may be disposed on adjacent and/or nonoverlapping regions of the shank (e.g., a first threaded region for engagement with bone and a second threaded region of different structure for locking to a locking element). The pitch of a thread may be constant along the shank, or may change either continuously or discretely according to position, For example, the pitch may decrease closer to a head of the fastener, to provide compression of the bone as the fastener is advanced into the bone. In some embodiments, the threaded shank may have two or more distinct threads with different pitches, such as a distal thread with a greater pitch, and a proximal thread with a lesser pitch, or vice versa. The proximal or the distal thread (or both) may be configured to be locked to a locking element.

In some embodiments, the thread of the threaded shank may have an at least substantially constant pitch along the shank. In these embodiments, the rate of advancement of the threaded shank into bone may be at least substantially equal to the rate of advancement of the threaded shank through the locking element. However, these rates may become unequal near the end of fastener installation if a locking element is capable of outward movement (e.g., see Example 2).

The threaded fasteners may have any suitable linear density of threads (or linear densities, if multithreaded). These densities may be measured using units, for example, such as number of threads per inch. For example, the fastener may have 16, 20, 24, 28, 32, 36, 40, and/or other numbers of threads per inch, among others; these linear densities correspond to thread-to-thread spacings (or pitches) of 0.0625 inches, 0.0500 inches, 0.0417 inches, 0.0357 inches, 0.03125 inches, 0.0278 inches, 0.0200 inches, and/or other fractions of an inch. In some embodiments, the threads on the fastener may have a continuously or discontinuously varying pitch at different positions along the fastener axis.

The threaded fasteners may have any suitable diameters, including major (crest-to-crest) and minor (root-to-root) diameters. In some embodiments, the major diameters may be between about 1 to 10 mm. Exemplary diameters include 1 mm, 1.5 mm, 2.0 mm, 2.7 mm, 3.5 mm, and 4.0 mm. In some embodiments, the difference between the major and minor diameters (generally, twice the thread height) may be in the range of about 0.1 mm to 5 mm, or in the range of about 0.2 mm to 2 mm. In some embodiments, the major diameter and minor diameter of the threaded shank may be generally the same along the length of the shank. In other embodiments, these diameters may be different in proximal and distal portions of the shank. For example, a proximal region of the shank (adjacent the head of the fastener) may have both a greater major and a greater minor diameter than a distal region of the shank, to permit selective coupling of the proximal region to a locking element.

Each fastener to be placed in a locking aperture may have a head. The head may lack (or include) a thread. In addition, the head may have any suitable tool engagement structure, such as a hexagonal socket, a single slot, a pair of slots in a cruciform arrangement, a polygonal projection, etc.

IV. Methods of Fixing Bones using Bone Plates with Movable Locking Elements

The systems provided by the present teachings may include methods of fixing bones by installing bone plates with locking elements on the bones. The methods may include any suitable combination of the following steps, performed in any suitable order, any suitable number of times, including once or a plurality of times for each step that is performed.

A bone plate may be selected for fixation of a bone having one or more discontinuities, such as a bone fractured or cut at one or more positions to create two or more bone fragments. The bone plate may have any suitable combination of the features described elsewhere in the present teachings. For example, the bone plate may include a plate body with one or more elongate openings, and one or more locking elements that can cooperate with the elongate openings to form one or more elongate locking apertures.

The fractured bone may be reduced. Reduction may be performed before, during, and/or after exposure of the bone surgically, in one step or a series of steps.

A plate body of the bone plate may be connected to a first portion of the bone (e.g., a first fragment(s) of a fractured or cut bone). The plate body may be connected (e.g., secured) to the first portion, before, during, and/or after reduction. (Plate bodies connected before or during reduction typically would be secured only partially to a target bone until the reduction is completed.) Connecting the plate body may be performed by placing one or more fasteners, such as screws, wires, pins, etc., through openings of the plate body and into the first portion of bone. Connection to the first portion of bone may be performed by placement of a fastener in a locking or nonlocking aperture that is elongate or non-elongate.

The plate body also may be connected to a second portion of the bone (e.g., a second fragment of a fractured or cut bone disposed on an opposing side of a discontinuity in the bone). The plate body may be connected to the second portion before or after the plate body is connected to the first portion. Connection of the plate body to the second portion of bone may include placing a threaded fastener through an elongate locking aperture of the bone plate. In particular, the threaded fastener may be placed through an oblong opening of the plate body and through a locking element disposed generally between the plate body and the second portion of bone. The oblong opening may be aligned with a through-hole of the locking element when the threaded fastener is placed through the locking aperture. Placement of the threaded fastener may lock the fastener to the locking element. In some embodiments, placement of the threaded fastener may connect the locking element to the plate body, such as when the locking element is a separate component that is not pre-connected to the plate body. Accordingly, placement of the fastener may be performed through the locking aperture before the plate body is disposed on bone.

The fastener, the locking element, and the second portion of bone may be moved collectively relative to the plate body and the first portion of bone while the fastener remains locked to the locking element. This movement may be performed by advancing the head of the fastener (e.g., by turning the fastener) against a wall of the elongate locking aperture with the fastener locked to the locking element. In addition, moving the second portion of bone relative to the first portion of bone may compress the bone longitudinally.

Further aspects of bone fixation with bone plates including elongate locking apertures are described elsewhere in the present teachings, such as in Sections I and V.

V. Examples

The following examples describe selected aspects and embodiments of the present teachings, particularly exemplary fixation systems including bone plates with movable locking elements and methods of using the bone plates to fix (and/or compress) bone. These examples and the various features and aspects thereof are included for illustration and are not intended to define or limit the entire scope of the present teachings.

Example 1

Elongate Locking Aperture with Selectable Screw Angles

This example describes an exemplary fixation system 110 including a bone plate 111 that permits locked placement of bone screws at a range of angles; see FIGS. 6 and 7.

FIG. 6 shows a bone screw 112 extending through an elongate locking aperture 114 of the bone plate and into bone 115. Bone screw 112 may be locked to a locking element 116 of the locking aperture. The locking element may be disposed in a cavity 118 formed below an opening 120 defined by a plate body 122 of the bone plate.

The cavity may include a chamber or hollow 124 to which the locking element is confined. The chamber may be defined above flanges 126 of the plate body. Chamber 124 may have a depth (or height) that is greater than the thickness of the locking element, such that the locking element may move up and down within the chamber (i.e., parallel to an axis extending between the inner and outer faces of the plate body (namely, a thickness axis of the plate body) and generally parallel to the long axis of the bone screw). Accordingly, the chamber may permit the locking element to move longitudinally along locking aperture 114 and transversely between the ceiling and floor of the chamber. In some embodiments, a chamber with a height greater than the thickness of the locking element may facilitate compression of the bone plate with bone (e.g., see Example 2).

FIG. 7 shows bone screw 112 pivoted from its orthogonal disposition of FIG. 6 to an oblique orientation. The height of chamber 124 may permit pivotal movement of the locking element within the chamber about axes extending through opposing sides and/or opposing ends of the plate body, such as a width axis defined by the plate body. The locking element may have a nonplanar surface(s) to facilitate the pivotal movement. For example, an outer surface 130 (and/or an inner surface 132) of the locking element may have a convex curved shape (e.g., a semispherical shape). In some examples, the inner surface of the locking element may be planar such that the locking element can be oriented relative to the plate body by contact with the floor of the chamber (namely, the top of flanges 126 in the present illustration). This defined orientation of the locking element may facilitate initial placement of the bone screw into the through-hole of the locking element with the bone screw square to the plate body, prior to pivoting the bone screw to a desired angle from orthogonal.

Pivotal movement of the locking element in a plane defined by the plate body (i.e., pivotal movement about an axis orthogonal to the plane) generally is restricted by engagement with an inner and/or outer wall of the plate body. Otherwise, the locking element would turn with the bone screw. Here, this pivotal movement is restricted by opposing lateral walls of the chamber.

Example 2

Elongate Locking Aperture with Biased Locking Element

This example describes an exemplary fixation system 150 including a bone plate 151 having a locking aperture 152 with a biased locking element 154; see FIGS. 8 and 9.

Locking element 154 may have a biasing mechanism 156 configured to position the locking element relative to a thickness axis 158 of a plate body 160 of the bone plate. In particular, the biasing mechanism may urge at least a portion of the locking element away from an outer face 162 and towards an inner face 164 of plate body 160. The biasing mechanism may be provided by one or more leaf springs created by tabs 166 extending with an angular disposition from a central region 168 of the locking element. The tabs may engage a ceiling surface 170 of a cavity 172 of the locking aperture. In addition, the tabs may be deformable to permit movement of the central region of the locking element generally parallel to thickness axis 158 of the plate body.

FIG. 8 shows an exemplary configuration of the locking element and plate body during installation of bone plate 151 on a bone 174. A bone screw 176 may extend through locking aperture 152, in threaded engagement with locking element 154, and with a top/outer surface 178 of the locking element spaced from ceiling 170 of cavity 172. In addition, inner face 164 of plate body 160 may be spaced slightly, indicated at 182, from an adjacent surface of bone 174. Alternatively, the plate body and/or locking element may be in contact with, but not tightly engaged with, the bone surface. In any case, the ability of the locking element to move upward in cavity 172 may allow the bone screw to function as a lag screw as the bone screw is rotated, indicated at 184, by a driver in FIG. 8. In particular, here, the bone screw is restricted from further advancement through the plate body by contact with a counterbore surface of the plate body. As a result, as the screw is turned the locking element and the bone may be urged upward, indicated at 186, toward the head of the bone screw, to compress, indicated at 188, the bone plate (and particularly the plate body) against the bone.

FIG. 9 shows bone plate 151 after bone screw 176 has been turned enough to compress the bone plate against bone. Plate body 160 may be tightly engaged with bone 174. In addition, locking element 154 may be deformed from its original configuration. For example, tabs 166 may be bent such that central region 168 of the locking element is repositioned in chamber 172, closer to the outer face of the plate body. In other examples, the locking element may be used in a similar way to compress the bone plate against bone, but may lack a biasing mechanism (e.g., see Example 1).

Example 3

Exemplary Bone Plate with Elongate Locking Apertures

This example describes an exemplary bone plate 210 with an array of elongate locking apertures; see FIGS. 10-12.

FIGS. 10-12 show an exploded view, an end view, and an inner (bottom) view, respectively, of bone plate 210. The bone plate may include a plate body or plate member 212, a plurality of locking elements 214, and stop members 216.

Plate body 212 may define various openings that receive fasteners (such as bone screws), locking elements 214, or stop members 216. These openings may include one or more elongate openings 218, channel 220, and post openings 222. The plate body also or alternatively may define one or more non-elongate (e.g., circular) openings configured to receive fasteners, such as bone screws, pins, or wires, among others.

Elongate openings 218 may be arrayed along the long axis of the plate body. These elongate openings may be configured to receive bone screws at a range of positions along a long axis 224 of each elongate opening. In addition, the elongate openings may have opposing sloped walls 226 with a camming action that couples net screw movements that are orthogonal and longitudinal relative to the plate body.

Channel 220 may act as a track configured to receive the locking elements and guide their sliding motion. The channel thus may extend along a portion or all of the length of the bone plate, so that the locking elements can be received from only one end, both ends, and/or an intermediate position of the plate body. The channel may have a width and/or a cross-sectional size and shape that are slightly larger than the width and/or cross-sectional size and shape of the locking elements, to permit sliding of the locking elements along the channel. In some examples, the channel may be configured to restrict orthogonal movement of locking elements. Accordingly, the channel may narrow toward the inner surface of the plate body. For example, in the present illustration, the channel has a dovetail shape that corresponds to the cross sectional shape of the locking elements (see FIG. 11).

Post openings 222 may be configured to receive stop members 216 that extend into channel 220. The stop members (e.g., posts) thus may be placed in the post openings after the locking elements have been received in the channel, to define a range of longitudinal motion for each locking element. FIG. 12 shows an exemplary range of motion, indicated at 228, for one of the locking elements. In addition, the stop members may restrict uncoupling of the locking elements from the plate body, by preventing the locking elements from sliding out of one or both ends of the bone plate. Assembly of the plate body with the locking elements and stop members may be performed at any time, for example, during manufacture of the bone plate.

Locking elements 214 may have any suitable configuration and may be present in a suitable number. Generally, the locking elements may be configured to engage bone screws threadably. Accordingly, the locking elements may be, for example, nuts or washers with a threaded bore 230 (e.g., see FIG. 11). Alternatively, the locking elements may include opposing lips that engage the thread of a bone screw (e.g., see Example 5). In some examples, such as in the present illustration, the bone plate may include a locking element for each elongate opening.

Each locking element may have any suitable arrangement of an inner surface 232 of the locking element. For example, the inner surface may project below the inner face of the plate body, as shown here, may be flush with the inner face, indicated by a dashed line at 234, or may be recessed, indicated by a dashed line at 236.

The stop members may have any suitable structure. For example, the stop members may be projections formed integrally with the plate body or may secured nonremovably or removably to the plate body, such as by welding, threaded engagement, an interference fit, a snap fit, and/or the like.

Example 4

Exemplary Approaches to Bone Plate Assembly

This example describes exemplary approaches for connecting locking elements to plate bodies to form bone plates with connected, movable locking elements; see FIGS. 13-17.

FIG. 13 shows a bottom view of an exemplary bone plate 250 including a plate body 252 and a locking element 254 that collectively form an elongate locking aperture 256. The plate body may define an elongate opening 258 and a cavity 260 adjoining the elongate opening. Furthermore, the plate body may have a pair of deformable tabs 262 providing inner walls of the cavity.

FIGS. 14 and 15 illustrate assembly of plate body 252 with locking element 254. FIG. 14 shows a cross-sectional view of the plate body with tabs 262 bent outward from cavity 260 to create a cavity mouth 264 that is wide enough to receive locking element 254. FIG. 15 shows assembled bone plate 250 after locking element 254 has been placed in cavity 260 and tabs 262 have been bent inward toward cavity 260 to close mouth 264 (see FIG. 14) and thus restrict removal of the locking element from the cavity.

FIG. 16 shows a pair of cross-sectional views of a bone plate 280, taken through an elongate locking aperture 282 of the bone plate in respective exploded and assembled configurations of the locking aperture. The bone plate may include a plate body 284 defining a cavity 286 with an inner face of the plate body. The cavity may be shaped for receiving a locking element, such as a nut 288, from a direction, indicated at 290, that is orthogonal to the inner face of the plate body. Accordingly, the cavity may have opposing inner walls 292, 294 that are parallel to one another. The locking element may be retained in the cavity by a retainer element 296 that contacts an inner surface 298 of the locking element to support the locking element and restrict its travel in a direction opposing that used for assembly. The retainer element may engage the opposing inner walls of the cavity, for example, being received in notches 300 defined by the inner walls. In addition, retainer element 296 may define a central opening 302 such that placement of the bone screw is not obstructed by the retainer element. The retainer element thus may be a plate, a clip (e.g., a C-clip), two or more discrete retainer elements extending into the cavity from respective lateral walls, and/or the like.

FIG. 17 shows respective exploded and assembled configurations of a bone plate 320 having an elongate locking aperture 322, with an inner face 324 (i.e., the bottom) of the bone plate facing up. Bone plate 320 may have a plate body 326 defining an elongate opening 328 and a cavity 330 adjoining the elongate opening. The cavity may have a mouth 332 for receiving a locking element 334 during assembly of the bone plate. In addition, the plate body may provide a retaining flange 336 extending into the cavity from opposing lateral walls thereof. Accordingly, the locking element may be placed into mouth 332 by movement orthogonal to a plane defined by the inner face of the plate body, and then moved longitudinally to position the locking element for retention by flange 336. In some embodiments, after the locking element has been placed into cavity 330, the mouth of the cavity may be obstructed and/or deformed to prevent removal of the locking element via the mouth. For example, the mouth may be obstructed by any material disposed in the mouth, either disposed removably (such as a removable fastener (e.g., a screw, a pin, a clip, etc.) or substantially permanently (such as an obstruction element attached to the plate body in the mouth of the cavity using an adhesive, welding, bonding, and/or the like). Alternatively, or in addition, the mouth may be altered in shape by deforming the cavity wall that defines the mouth. For example, here, a tab 338 of the cavity wall is deformed (compare the tab configuration on the left and right sides of FIG. 17).

Example 5

Exemplary Bone Plate with External Locking Elements

This example describes an exemplary bone plate 350 with external locking elements; see FIGS. 18-23.

FIG. 18 shows bone plate 350 from the side at an intermediate stage of assembly; FIG. 19 shows a fragmentary sectional view of the bone plate. The bone plate may include one or more external locking elements 352. Bone plate 350 also may include a plate body 354 defining a plurality of elongate openings 356. Each elongate opening may be aligned with a locking element, particularly a through-hole 358 defined by the locking element (see FIG. 19) to collectively form elongate locking apertures 360.

The plate body may define tracks 362 disposed on opposing sides of the plate body. Tracks 362 may be structured to receive opposing portions of each locking element, as the locking element is placed onto the plate body. For example, the tracks may be formed by longitudinal grooves 364 extending any suitable portion of the length of the plate body.

The locking element may be received over the plate body such that the locking element is at least mostly external to the plate body. For example, the locking element may be a clip having opposing hook portions 366, 368 (and/or flanges) that connect the locking element to the plate body (see FIG. 19), namely, by being received in longitudinal grooves 364. In any case, the hook portions may extend laterally beyond an inner face 370 of the plate body, at least partially over opposing side/lateral surfaces 372 of the plate body. The hook portions may terminate adjacent the side surfaces, as shown here, or may extend to an outer face 374 of the plate body. The hook portions may flank a central region 376 of the locking element that defines through-hole 358 and that extends generally parallel to inner face 370 of the plate body.

Each locking element may be placed onto the plate body by longitudinal motion along the plate body. Here, the locking aperture on the right in FIG. 18 has been formed by positioning a locking element under an elongate opening, and a locking aperture on the left may be created when the locking element is advanced to a position under the leftward elongate opening of the plate body.

One or more of tracks 362 may determine the permitted longitudinal range of motion of each locking element and/or may restrict inadvertent removal of locking elements from the plate body. For example, track 362 may have a nonuniform width that creates a plurality of shoulders or stops 378 along the track (see FIG. 18). In some embodiments, track 362 may flare, indicated at 380, to provide an entry site(s) at which a locking element may be placed initially into track 362.

One or more tabs 382 of each locking element may engage stops 378 to restrict longitudinal motion of the locking element. The tabs may be elastic, to allow advancement of the locking element past a stop. In particular, the tabs may be pushed towards the hook portion of the locking element as the locking element is advanced along narrowed regions of the track, and then may spring outward (upward in this view) toward their unbiased positions where the track widens. Accordingly, each locking element may have a permitted range of longitudinal motion defined by a one or at least a pair of stops and one or at least a pair of tabs of a locking element. For example, the locking element indicated at 384 may have a range of motion substantially restricted to a corresponding region under elongate opening 356 of the plate body. Locking elements may be removed from the bone plate and/or moved between positions below distinct elongate openings of the plate body by urging tabs 382 away from their biased, retaining positions. For example, the tabs may be engaged with a tool that moves the tabs away from the retaining configuration in which they contact stops.

Plate body 354 may have recessed regions 390, 392 defined by the inner face of the plate body. Each recessed region may be disposed under an elongate opening of the plate body and may be sized to receive a central region of a locking element. In particular, the recessed region may have a depth that is at least about as great as, or greater than, the thickness of the central region of a locking element. In addition, the recessed region may have a length, measured longitudinally along the plate body, that is greater than the corresponding dimension of the locking element, to permit the locking element to slide longitudinally along the recessed region.

Figure 20:
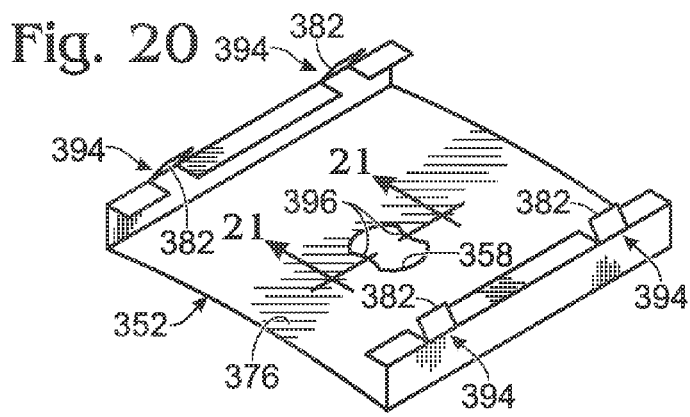
FIG. 20 is a view of the locking element of FIG. 19, taken generally as in FIG. 19, but in the absence of the plate body.

FIG. 20 shows locking element 352 separated from the plate body. Locking element 352 may have any suitable composition and features. The locking element may be formed, for example, of a sheet that is metal, plastic, a bioresorbable material, and/or the like. In exemplary embodiments, the locking element may be formed of a metal sheet that is bent to create the hook portions and cut to create through-hole 358 and one or more biasing mechanisms 394.

Each biasing mechanism may have any suitable structure and function. For example, the biasing mechanism may be created by tab 382. The biasing mechanism(s) may operate to space central region 376 and thus through-hole 358 from the inner face of the plate body when a bone screw is placed initially into engagement with the locking element (see below). The biasing mechanism may be overcome when the bone screw is tightened against the plate body, to decrease the spacing between the central region of the locking element and the inner face of the bone plate, to provide compression of the plate body and bone (e.g., generally as described above in Example 2). The biasing mechanism also may be part of a stop mechanism that functions to retain the locking element in general alignment with an elongate opening of the plate body as described above.

Through-hole 358 may have any suitable structure that promotes locking engagement with a threaded fastener. For example, the through-hole may have opposing lips or projections 396 that selectively engage a thread of a fastener (see FIG. 21).

Figure 21:
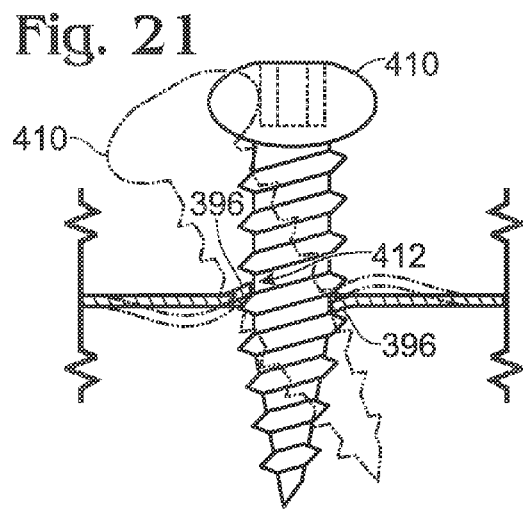
FIG. 21 is a sectional view of the locking element of FIG. 20, taken generally along line 21-21 of FIG. 20 with a bone screw disposed in threaded engagement with the locking element and illustrating distinct orientations of the bone screw permitted by flexing the locking element.

FIG. 21 shows a sectional view taken through the locking element (particularly through-hole 358) with a bone screw 410 in threaded engagement with the locking element. Lips 396 may be offset from one another in a direction orthogonal to a plane defined by the locking element, i.e., bent out of the plane in correspondence with the thread pitch of the bone screw. For example, lips 396 may be offset by about one-half the pitch or a multiple thereof. The locking element may have any suitable thickness. In some cases, the thickness of the locking element may be about the same as the thickness of the lips, or the thicknesses may be different. Furthermore, the thickness of the lips and/or locking element may be substantially less than the pitch of the bone screw such that the lips fit into the thread groove of the bone screw, as indicated at 412. In other embodiments, an external locking element may have a preformed internal thread and/or may have a thread-like structure formed as the locking element is deformed and/or cut by placement of the bone screw into the through-hole of the locking element.

The external locking element may be deformable to accommodate a range of orientations of the bone screw. For example, the bone screw may be pivoted to an oblique orientation (shown here in phantom outline), which may be allowed by altering the general shape of the central region of the locking element and/or by bending the lips of the locking element, among others. The angle of the bone screw may be selected before and/or after the bone screw is engaged with the locking element, and generally before the bone screw is advanced into bone.

Figure 22:
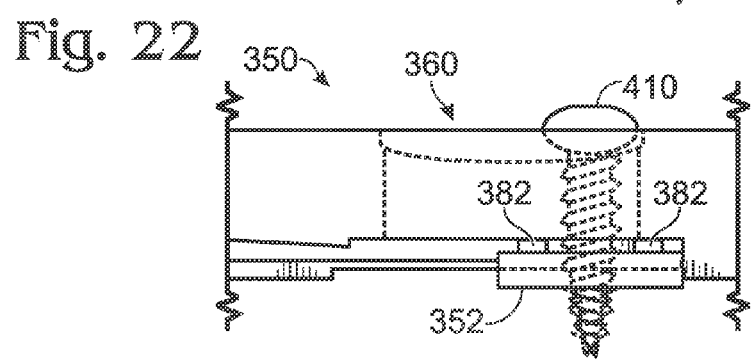
FIG. 22 is a fragmentary side view of the bone plate of FIG. 18, taken generally around an elongate locking aperture of the bone plate, with a bone screw locked in the locking aperture but not fully seated, in accordance with aspects of the present teachings.
Figure 23:
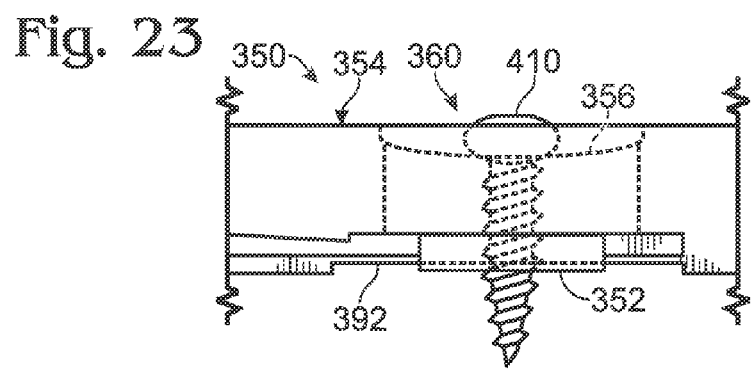
FIG. 23 is a fragmentary side view of the bone plate of FIG. 18, taken as in FIG. 22, with the bone screw fully advanced to a seated position in the locking aperture such that the locking element of the locking aperture has moved upward in relation to the plate body of the bone plate, to the compress the bone plate against bone, in accordance with aspects of the present teachings.

FIGS. 22 and 23 collectively illustrate how a locking element 352 of bone plate 350 may be repositioned as bone screw 410 is tightened against the plate body of the bone plate. FIG. 22 shows bone screw 410 installed in elongate locking aperture 360, but not fully advanced and seated in the aperture. In this configuration, the bone screw may be disposed toward one end of the locking aperture and locking element 352 may be urged away from the recessed region of the inner face via tabs 382. FIG. 23 shows bone screw 410 tightened to a seated position in locking aperture 360, namely, a more central position longitudinally within elongate opening 356 produced by relative movement of the locking element and plate body 354. The locking element may be pulled into recessed region 392 by tightening the bone screw, thereby bringing connected bone into contact and/or tighter engagement with the inner face of the plate body of the bone plate.

Example 6

Selected Embodiments

This example describes selected embodiments of the present teachings, presented as a series of indexed paragraphs.

1. A bone plate for bone fixation, comprising: (A) a plate member including a plurality of openings, at least one of the plurality of openings being an elongate opening configured to receive a fastener that affixes the plate member to bone, the elongate opening defining a long axis; and (B) a locking element configured to be received at least partially by the plate member such the locking element can move slidably generally parallel to the long axis, the locking element having a through-hole for receiving the fastener from the elongate opening such that the fastener is engaged and retained by the locking element in a configuration that permits additional advancement of the fastener through the through-hole.

2. The bone plate of paragraph 1, wherein the elongate opening has a counterbore surface configured to couple rotation of the fastener against the counterbore surface to motion of the fastener along the long axis of the elongate opening.

3. The bone plate of paragraph 1 or 2, wherein at least one of the plurality of openings does not have a corresponding locking element.

4. The bone plate of any of paragraphs 1-3, further comprising one or more stop elements that restrict travel of the locking element in at least one direction generally parallel to the long axis of the elongate opening.

5. The bone plate of paragraph 4, wherein the one or more stop elements include a pair of stop elements that restrict travel of the locking element in opposing directions parallel to the long axis of the elongate opening.

6. The bone plate of any of paragraphs 1-5, the plate member having opposing end regions, wherein the plate member defines a longitudinal recess or cavity configured to receive the locking element from one or both opposing end regions.

7. The bone plate of paragraph 6, wherein the plate member has an outer surface, and wherein the longitudinal recess or cavity narrows in a direction generally orthogonal to and inward from the outer surface such that the locking element received in the longitudinal recess or cavity is restricted from substantial movement in the direction.

8. The bone plate of any of paragraphs 1-7, wherein the plate member has an inner surface that faces bone, and wherein the inner surface defines a track along which the locking element can slide adjacent the inner surface.

9. The bone plate of paragraph 8, wherein the plate member includes projections extending from the inner surface, and wherein the projections define the track.

10. The bone plate of any of paragraphs 1-9, wherein the locking element is coupled to the plate member such that sliding motion of the locking element is at least substantially restricted to opposing directions generally parallel to the long axis of the elongate opening.

11. The bone plate of any of paragraphs 1-10, wherein the plate member defines a longitudinal axis, and wherein the long axis of the elongate aperture and the longitudinal axis of the plate member are at least substantially parallel.

12. The bone plate of any of paragraphs 1-11, wherein the locking element is coupled to the plate member such that pivotal motion of the locking element is substantially restricted.

13. The bone plate of any of paragraphs 1-12, wherein the locking element includes an internal thread.

14. The bone plate of any of paragraphs 1-13, wherein the plate member includes opposing longitudinal sides flanking an inner surface, and wherein the locking element extends laterally beyond the inner surface to positions adjacent each of the opposing longitudinal sides.

15. The bone plate of any of paragraphs 1-14, wherein the plate member is formed of a biocompatible material.

16. The bone plate of any of paragraphs 1-15, wherein the plate member and the locking element are formed of different materials.

17. A method of bone fixation, comprising: (A) selecting a plate member for fixing a bone; (B) placing a fastener through an elongate opening of the plate member, into locked engagement with a locking element disposed toward bone from the elongate aperture, and into a portion of the bone; and (C) advancing a head of the fastener against a wall of the elongate opening while the locking element is disposed in locked engagement with the locking element, such that the fastener and the portion of bone are urged substantially parallel to a long axis defined by the elongate aperture, thereby adjusting fixation of the bone.

18. The method of paragraph 17, the plate member and the bone each having a long axis, further comprising a step of disposing the plate member on the bone such that the long axes of the plate member and the bone are generally parallel.

19. The method of paragraph 17 or 18, wherein the step of advancing compresses the bone longitudinally.

20. The method of any of paragraphs 17-19, the bone having a discontinuity, further comprising a step of coupling the bone plate to the bone on opposing sides of the discontinuity before the step of advancing.

21. The method of any of paragraphs 17-20, wherein the steps of placing and advancing are performed at least twice with at least two elongate openings such that the bone is urged incrementally along the at least two elongate openings.

22. A kit for bone fixation, comprising: (A) the bone plate of any of paragraphs 1-16; and (B) at least one fastener configured to be received in the elongate opening, to be locked to the locking element, and to extend into bone.

23. A bone plate for bone fixation, comprising: (A) a plate body defining a plurality of openings for receiving fasteners that secure the plate body to bone; and (B) a locking element defining a through-hole for receiving a threaded region of a fastener that extends through an opening of the plate body, such that the threaded region of the fastener is in threaded engagement with the locking element, the locking element being connected movably to the plate body in the absence of the fastener.

24. The bone plate of paragraph 23, wherein the opening is oblong and defines a long axis, and wherein the locking element is slidable along the long axis.

25. The bone plate of paragraph 24, wherein the opening includes a countersink surface configured to couple advancement of the fastener against the countersink surface with motion of the fastener along the long axis of the opening.

26. The bone plate of any of paragraphs 23-25, the locking element being a first locking element, further comprising one or more additional locking elements that form a set of locking elements collectively with the first locking element, wherein the set of locking elements is connected to the plate body, and wherein each locking element is movable individually.

27. The bone plate of any of paragraphs 23-26, wherein the plate body has a long axis and a length measured parallel to the long axis, wherein the locking element is capable of sliding motion generally along the long axis, limited to only a subset of the length.

28. The bone plate of any of paragraphs 23-27, the plate body having opposing inner and outer surfaces, wherein the inner surface defines a cavity in which the locking element is at least mostly received, and wherein the locking element is retained in the cavity by the plate body, in the absence of the threaded fastener, when the inner surface is facing downward.

29. The bone plate of any of paragraphs 23-28, wherein the plate body has opposing lateral sides flanking opposing inner and outer faces, wherein the locking element is disposed adjacent the inner face and extends beyond the inner face at least to a position adjacent each opposing lateral side.

30. The bone plate of any of paragraphs 23-29, wherein the locking element includes a sheet of material having opposing flanges, and wherein the plate body defines a pair of grooves for receiving the opposing flanges.

31. The bone plate of paragraph 30, wherein the sheet of material is a bent metal sheet.

32. The bone plate of any of paragraphs 23-31, wherein the locking element includes opposing hook structures that connect the locking element to the body.

33. The bone plate of any of paragraphs 23-32, wherein the locking element is capable of sliding motion that is at least substantially restricted to opposing directions generally parallel to a long axis of the plate body.

34. The bone plate of any of paragraphs 23-32, wherein the plate member defines a plane, and wherein the locking element is capable of a substantial movement orthogonal to the plane, and wherein the locking element is capable of pivotable motion out of the plane that permits the threaded fastener to be disposed in locked engagement with the locking element while at different angles relative to the plate body.

35. The bone plate of any of paragraphs 23-34, the plate body defining a plane, wherein the locking element is substantially restricted from in-plane pivotal motion.

36. The bone plate of any of paragraphs 23-35, wherein the locking element is configured to be deformed by advancement of the threaded fastener such that the locking element is repositioned relative to the plate body.

37. The bone plate of any of paragraphs 23-36, wherein the locking element has opposing upper and lower surfaces, and wherein at least one of the upper and lower surfaces is semispherical.

38. The bone plate of any of paragraphs 23-37, wherein the locking element has a biased position in relation to the plate body.

39. A method of bone fixation, comprising: (A) selecting a bone plate including a plate body and a locking element; (B) connecting the bone plate to a first portion of the bone; (C) placing a fastener into a second portion of the bone through an oblong opening of the plate body and also through a through-hole of the locking element such that the fastener is in threaded engagement with the locking element; and (D) advancing the fastener against an inclined surface of the plate body adjacent the oblong opening such that the fastener, the locking element, and the second portion of the bone are urged collectively in a direction parallel to the oblong opening.

40. A method of bone fixation, comprising: (A) connecting a plate body of a bone plate to a first portion of bone; (B) placing a fastener into a second portion of bone from an oblong opening of the plate body and through a locking element disposed generally between the plate body and the second portion of bone, such that the fastener connects the bone plate to the second portion of bone and is locked to the locking element; and (C) moving the fastener, the locking element, and the second portion of bone collectively relative to the plate body and the first portion of bone, to urge the first and second portions of bone toward one another while the fastener remains locked to the locking element.

41. The method of paragraph 40, wherein the steps of connecting, placing, and moving are performed with a fractured bone.

42. The method of paragraph 40 or 41, wherein the step of connecting is performed before the step of placing.

43. The method of any of paragraphs 40-42, wherein the step of placing includes a step of placing a bone screw.

44. The method of any of paragraphs 40-43, wherein the step of placing includes a step of placing a fastener having a semispherical head.

45. The method of any of paragraphs 40-44, wherein the step of moving includes a step of turning the fastener.

46. The method of any of paragraphs 40-45, wherein the step of connecting includes a step of connecting the plate body to the bone via a first region of the plate body, wherein the oblong opening has opposing ends disposed respectively closer to and farther from the first region of the plate body, and wherein the step of placing is performed with the locking element disposed toward one end that is farther from the first region of the plate body.

47. A bone plate for bone fixation, comprising: (A) a plate body defining a plurality of openings for receiving fasteners that secure the plate body to bone, the plurality of openings including an oblong opening defining a long axis; and (B) a locking element configured to be disposed in threaded engagement with a fastener extending at least from the oblong opening, then through the locking element and into bone, such that the locking element contacts the plate body and is slidable parallel to the long axis of the oblong opening.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A bone plate for bone fixation, comprising:
a plate body defining a longitudinal axis and a pair of grooves, wherein the pair of grooves extend parallel to the longitudinal axis; and
a locking element including a portion having a through-hole with an internal thread and also including a biasing mechanism that resiliently positions the portion having a through-hole with respect to the plate body, the locking element being configured to receive a fastener in the through-hole such that the fastener is in threaded engagement with the internal thread, the locking element being disposed in the pair of grooves for movement along the grooves in a direction parallel to the longitudinal axis.

2. The bone plate of claim 1, wherein the portion having a through-hole and a portion of the locking element that forms the biasing mechanism are continuous with one another.

3. The bone plate of claim 1, wherein the plate body has an inner surface region configured to face bone, and wherein the locking element has a biased position with respect to the plate body along an axis that is at least generally orthogonal to the inner surface region.

4. The bone plate of claim 1, wherein the locking element is a first locking element, further comprising a second locking element y disposed in a pair of grooves defined by the plate body.

5. The bone plate of claim 1, wherein the locking element is removable from the plate body.

6. The bone plate of claim 1, wherein the pair of grooves are internal grooves located inside the plate body.

7. A bone plate for bone fixation, comprising:
a plate body defining a longitudinal axis and an opening, the plate body including flanges that border the opening and extend parallel to the longitudinal axis; and
a spring-biased element supported by the flanges and movable along the flanges in a direction parallel to the longitudinal axis, the spring-biased element being configured to receive a fastener in threaded engagement with the spring-biased element.

8. The bone plate of claim 7, wherein the spring-biased element includes a flexible portion.

9. The bone plate of claim 7, wherein the plate body has an inner surface region configured to face bone, and wherein the spring-biased element has a biased position with respect to the plate body along an axis that is at least generally orthogonal to the inner surface region.

10. The bone plate of claim 7, wherein the spring-biased element is removable from the plate body.

11. A method of fixing bone, the method comprising:
selecting a bone plate including a plate body defining a longitudinal axis, the plate body including a pair of tracks that extend parallel to the longitudinal axis, the bone plate including a spring-biased locking element disposed in the pair of tracks and slidable along the pair of tracks in a direction parallel to the longitudinal axis; and
attaching the bone plate to bone with a fastener extending into the bone and disposed in threaded engagement with the locking element.

12. The method of claim 11, wherein the locking element is a first locking element and the bone plate includes a second spring-biased locking element, further comprising a step of attaching the bone plate to the bone with another fastener extending into the bone and locked to the second spring-biased locking element.

13. The method of claim 11, further comprising a step of sliding the locking element with respect to the plate body in the direction parallel to the longitudinal axis.

* * * * *